US012788292B2

(12) United States Patent
Morita et al.

(10) Patent No.: US 12,788,292 B2
(45) Date of Patent: Nov. 10, 2026

(54) INFORMATION PROCESSING METHOD, INFORMATION PROCESSING SYSTEM, AND RECORDING MEDIUM

(71) Applicant: Panasonic Intellectual Property Management Co., Ltd., Osaka (JP)

(72) Inventors: Yukihiro Morita, Osaka (JP); Shinnosuke Hirokawa, Osaka (JP); Yuichi Kobayakawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 174 days.

(21) Appl. No.: 18/770,128

(22) Filed: Jul. 11, 2024

(65) Prior Publication Data

US 2024/0358304 A1 Oct. 31, 2024

Related U.S. Application Data

(63) Continuation of application No. PCT/JP2022/047743, filed on Dec. 23, 2022.

(30) Foreign Application Priority Data

Jan. 25, 2022 (JP) ................................ 2022-009629

(51) Int. Cl.
*A61B 5/16* (2006.01)
*A61B 5/00* (2006.01)
(Continued)

(52) U.S. Cl.
CPC .......... *A61B 5/165* (2013.01); *A61B 5/02405* (2013.01); *A61B 5/441* (2013.01);
(Continued)

(58) Field of Classification Search
CPC ..... A61B 5/165; A61B 5/02405; A61B 5/441; G16H 20/70; G06V 40/15; G06V 40/16;
(Continued)

(56) References Cited

U.S. PATENT DOCUMENTS

2014/0161421 A1* 6/2014 Shoemaker ............ G11B 27/28 386/278
2019/0114934 A1 4/2019 Asa et al.
(Continued)

FOREIGN PATENT DOCUMENTS

JP 2013-017722 1/2013
JP 2019-072371 5/2019
(Continued)

OTHER PUBLICATIONS

Mustafa et al., "Heart Rate Estimation From Facial Videos for Depression Analysis," 2017 Seventh International Conference on Affective Computing and Intelligent Interaction (ACII). (Year: 2017).*
(Continued)

*Primary Examiner* — Jonathon A. Szumny
(74) *Attorney, Agent, or Firm* — Greenblum & Bernstein, P.L.C.

(57) ABSTRACT

An information processing method that is executed by one or more computers includes: acquiring first biological information of a first user and second biological information of a second user; determining, on the basis of the first biological information, whether the first user is in a state of stress; (i) in a case where it is determined that the first user is not in the state of stress, outputting first degree-of-empathy information that is information generated on the basis of the first biological information and the second biological information and that indicates a degree of empathy between the first user and the second user; and (ii) in a case where it is
(Continued)

determined that the first user is in the state of stress, outputting second degree-of-empathy information that indicates a degree of empathy that is higher than the degree of empathy indicated by the first degree-of-empathy information.

8 Claims, 18 Drawing Sheets

(51) Int. Cl.
*A61B 5/024* (2006.01)
*G06V 40/10* (2022.01)
*G06V 40/16* (2022.01)
*H04L 65/403* (2022.01)

(52) U.S. Cl.
CPC .............. *G06V 40/15* (2022.01); *G06V 40/16* (2022.01); *G06V 40/172* (2022.01); *H04L 65/403* (2013.01); *G06F 2203/011* (2013.01)

(58) Field of Classification Search
CPC ....................... G06V 40/172; G06F 2203/011; H04L 65/403
See application file for complete search history.

(56) References Cited

U.S. PATENT DOCUMENTS

2021/0076002 A1* 3/2021 Peters .................... H04N 7/152
2023/0363680 A1* 11/2023 Shimizu ............... G06V 40/174

FOREIGN PATENT DOCUMENTS

JP 2020187510 A * 11/2020
KR 102285482 B1 * 8/2021 ......... H04N 21/4662
WO WO-2014040175 A1 * 3/2014 ........... A61B 5/0006
WO WO-2020003910 A1 * 1/2020 ......... A61B 5/02416
WO WO-2022145811 A1 * 7/2022 ............. A61B 5/486

OTHER PUBLICATIONS

International Search Report of PCT application No. PCT/JP2022/047743 dated Feb. 21, 2023.

* cited by examiner (a)

(b)

(a)

| COEFFICIENT OF CORRELATION r | CORRELATION STRENGTH |
|---|---|
| $r \leq 0.2$ | (ALMOST) NOT CORRELATED |
| $0.2 < r \leq 0.4$ | WEAKLY CORRELATED |
| $0.4 < r \leq 0.7$ | CORRELATED |
| $0.7 < r \leq 0.9$ | STRONGLY CORRELATED |
| $0.9 < r \leq 1.0$ | (ALMOST) COMPLETELY CORRELATED |

(b)

| | | | |
|---|---|---|---|
| AMOUNT OF CHANGE IN RRI | ↓↓ | ↑ | → |
| AMOUNT OF CHANGE IN CvRR | ↑↑ | → | ↓↓ |
| FACTOR OF STRESS | INTERPERSONAL FACTOR | PAIN | COGNITIVE FATIGUE |

| | | | |
|---|---|---|---|
| AMOUNT OF CHANGE IN RRI | ↓ | ↑ | → |
| AMOUNT OF CHANGE IN CvRR | ↑ | → | ↓ |
| AMOUNT OF CHANGE IN SC | ↑ | ↑ | → |
| FACTOR OF STRESS | INTERPERSONAL FACTOR | PAIN | COGNITIVE FATIGUE |

INFORMATION PROCESSING METHOD, INFORMATION PROCESSING SYSTEM, AND RECORDING MEDIUM

BACKGROUND

1. Technical Field

The present disclosure relates, for example, to an information processing method involving the use of biological information.

2. Description of the Related Art

Conventionally, there has been proposed an information processing method for evaluating an extent of empathy between a plurality of persons with the use of biological information of the plurality of persons. For example, Japanese Patent No. 5280494 discloses an information processing method for evaluating an extent of empathy by near-infrared spectroscopy (NIRS). Japanese Unexamined Patent Application Publication No. 2019-072371 discloses an information processing method for calculating a degree of empathy with the use of a state feature calculated on the basis of a biological signal acquired by a device such as a microphone or a camera.

SUMMARY

However, the information processing methods disclosed in Japanese Patent No. 5280494 and Japanese Unexamined Patent Application Publication No. 2019-072371 have room for improvement in terms of communication.

One non-limiting and exemplary embodiment provides an information processing method that makes it possible to more smoothly perform communication.

In one general aspect, the techniques disclosed here feature an information processing method that is executed by one or more computers, the information processing method including: acquiring first biological information of a first user and second biological information of a second user; determining, on the basis of the first biological information, whether the first user is in a state of stress; (i) in a case where it is determined that the first user is not in the state of stress, outputting first degree-of-empathy information that is information generated on the basis of the first biological information and the second biological information and that indicates a degree of empathy between the first user and the second user; and (ii) in a case where it is determined that the first user is in the state of stress, outputting second degree-of-empathy information that indicates a degree of empathy that is higher than the degree of empathy indicated by the first degree-of-empathy information.

The information processing method of the present disclosure makes it possible to more smoothly perform communication.

It should be noted that general or specific embodiments may be implemented as a system, a method, an integrated circuit, a computer program, a storage medium, or any selective combination thereof. Further, the storage medium may be a non-transitory storage medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTIONS

Figure 1:
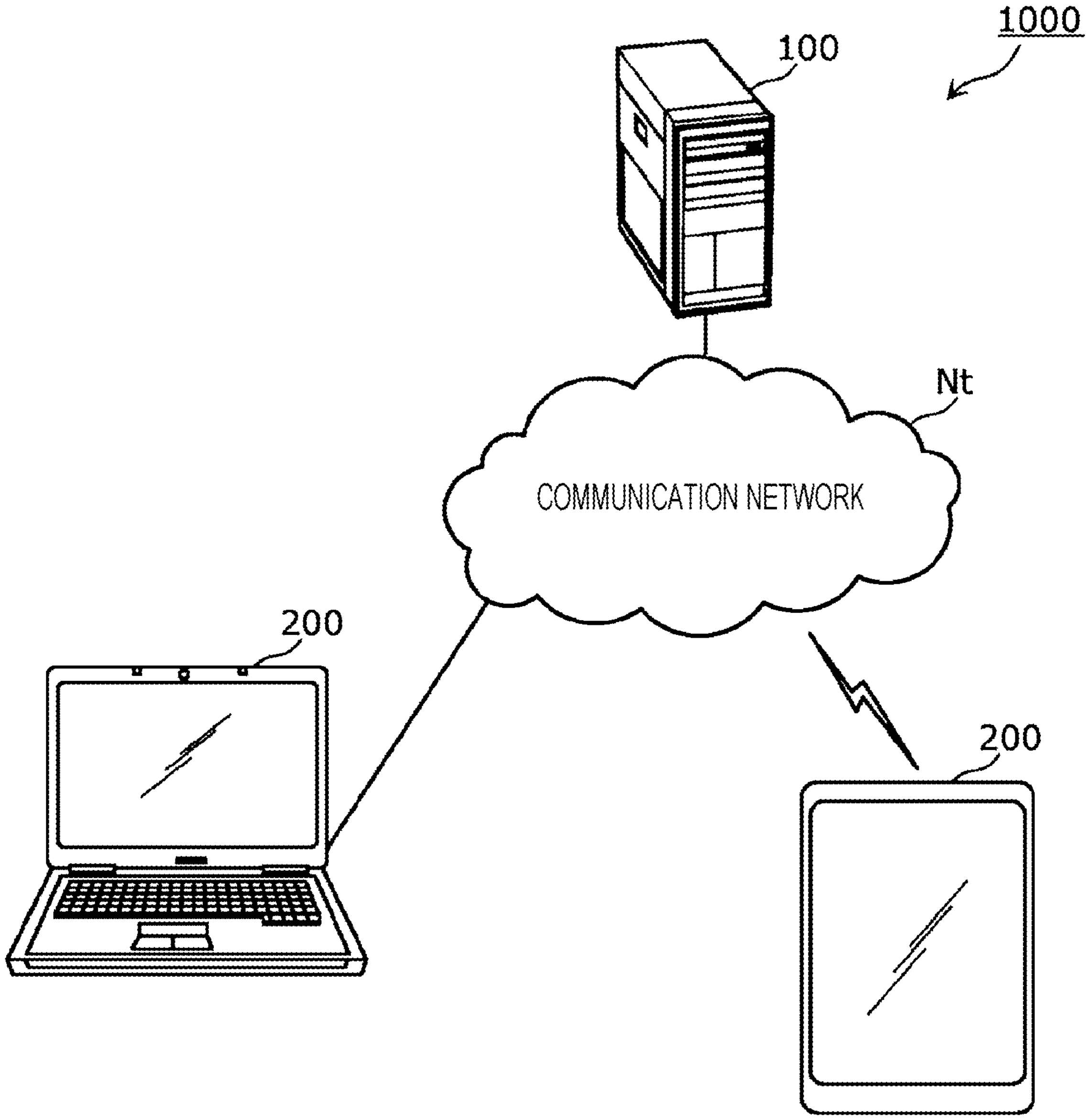
FIG. 1 is a diagram showing a configuration of an information processing system according to an embodiment.

Underlying Knowledge Forming Basis of the Present Disclosure

For reduction of risk of viruses or infectious diseases such as novel coronaviruses, online communication is rapidly expanding worldwide. With the spread of telecommuting, face-to-face conferences have been replaced by online conferences, and it has been become difficult to perform face-to-face communication performed to date. Moreover, there have been an increasing number of opportunities to perform online communication involving the utilization of Zoom (registered trademark), Teams (registered trademark), or other web conferencing tools.

When a plurality of persons perform face-to-face communication, each person performs communication by obtaining various pieces of information on that occasion with his/her fives senses and grasping the states of the other persons including subtle nuances. Meanwhile, when a plurality of persons perform online communication, each person can only obtain a considerably smaller amount of information on the states of the other persons than he/she would when performing face-to-face communication. This results in making it difficult to properly perform communication and causes various communication problems such as each person missing an opportunity to speak and being unable to understand the real intension of remarks made by the other persons. Further, since each person cannot properly grasp the states of the other persons while he/she is speaking, he/she has no way of knowing whether the other persons empathize with his/her remarks. This results in such a big communication problem that each person cannot have exhaustive discussions with the other persons. Further, for example, in a case where a speaker delivers a message to a large number of listeners, there can be a problem such as the speaker being unable to grasp whether the listeners understand the content of his/her message.

To address this problem, for example, presenting a degree of empathy makes it possible to increase the possibility of facilitating communication. In a specific example, a first participant and a second participant participate in online communication in which the first participant speaks and the second participant listens to the first participant speaking. In such a case, a degree of empathy that represents the extent to which the second participant empathizes with the first participant is presented to the first participant. This allows the first participant to grasp whether the second participant empathizes with his/her remarks, thus making it easy to facilitate communication.

However, on the other hand, in a case where the degree of empathy thus presented is low, it may make communication difficult. In the aforementioned example, if a low degree of empathy is presented to the first participant in a case where the first participant is tense, there is an increase in extent of tension of the first participant, so that it becomes difficult for the first participant to communicate with the second participant. Alternatively, if a low degree of empathy is presented to the first participant in a case where the first participant and the second participant communicate with each other for the first time, the first participant is at a loss how he/she should speak to the second participant, so that it becomes difficult to communicate with the second participant.

In one general aspect, the techniques disclosed here feature an information processing method that is executed by one or more computers, the information processing method including: acquiring first biological information of a first user and second biological information of a second user; determining, on the basis of the first biological information, whether the first user is in a state of stress; (i) in a case where it is determined that the first user is not in the state of stress, outputting first degree-of-empathy information that is information generated on the basis of the first biological information and the second biological information and that indicates a degree of empathy between the first user and the second user; and (ii) in a case where it is determined that the first user is in the state of stress, outputting second degree-of-empathy information that indicates a degree of empathy that is higher than the degree of empathy indicated by the first degree-of-empathy information. The first user and the second user are each a person who uses the one or more computers.

According to this, for example, when online communication involving the use of one or more computers is being performed, information that indicates a degree of empathy between a first user and a second user of a plurality of participants in the online communication is outputted. The information is first degree-of-empathy information or second degree-of-empathy information. Accordingly, presenting the degree of empathy between the first user and the second user to the first user, i.e. feeding back the degree of empathy to the first user, allows the first user to properly grasp the state of the second user to facilitate communication.

Furthermore, when the first user is in the state of stress, a degree of empathy that is higher than an actual degree of empathy that is the degree of empathy indicated by the first degree-of-empathy information is fed back to the first user. The state of stress is, for example, a state of tension. On the other hand, feeding back the actual low degree of empathy to the first user when the first user is in the state of stress may cause an increase in extent of the state of stress of the first user and make communication difficult. However, in the information processing method according to the aspect of the present disclosure, as mentioned above, when the first user is in the state of stress, the degree of empathy that is higher than the actual degree of empathy is fed back to the first user. This suppresses the increase in extent of the state of stress of the first user, making it possible to more smoothly perform communication.

Further, the information processing method may further include: acquiring relationship information that indicates a relationship between the first user and the second user; and determining, on the basis of the relationship information, whether the relationship between the first user and the second user is good. Outputting the second degree-of-empathy information may include outputting the second degree-of-empathy information in a case where it is determined that the first user is in the state of stress and it is determined that the relationship is not good.

According to this, when the first user is in the state of stress and does not have a good relationship with the second user (i.e. is in a state of poor relationship), a degree of empathy that is higher than an actual degree of empathy that is the degree of empathy indicated by the first degree-of-empathy information is fed back to the first user. On the other hand, feeding back the actual low degree of empathy to the first user when the first user is in the state of poor relationship may cause an increase in extent of bewilderment of the first user with respect to the second user in communication and make communication difficult. However, in the information processing method according to the aspect of the present disclosure, as mentioned above, when the first user is in the state of stress and the state of poor relationship, the degree of empathy that is higher than the actual degree of empathy is fed back to the first user. This suppresses the increases in extent of the state of stress and extent of bewilderment of the first user, making it possible to more smoothly perform communication.

Further, the relationship information may indicate at least one of a number, duration, frequency, or content of conversations between the first user and the second user as the relationship.

According to this, using the relationship information makes it possible to properly determine whether the relationship between the first user and the second user is good.

Further, in a case where the relationship information indicates the number of conversations, determining the relationship may include, when the number of conversations is smaller than a threshold, determining that the relationship is not good and, when the number of conversations is larger than or equal to the threshold, determining that the relationship is good.

This makes it possible to quantitatively properly determine whether the relationship between the first user and the second user is good.

Further, outputting the first degree-of-empathy information may include generating the first degree-of-empathy information with use of a first algorithm, and outputting the second degree-of-empathy information may include generating the second degree-of-empathy information with use of a second algorithm that is different from the first algorithm. For example, generating the second degree-of-empathy information may include generating the second degree-of-empathy information in accordance with the second algorithm by which a positive numerical value is added to the degree of empathy indicated by the first degree-of-empathy information.

This makes it possible to properly make the degree of empathy indicated by the second degree-of-empathy information higher than the degree of empathy indicated by the first degree-of-empathy information and feed back the degree of empathy indicated by the second degree-of-empathy information to the first user.

Further, the information processing method may further include: storing the first degree-of-empathy information and the second degree-of-empathy information on a storage medium; and generating difference information that indicates a difference between the degree of empathy indicated by the first degree-of-empathy information stored on the storage medium and the degree of empathy indicated by the second degree-of-empathy information stored on the storage medium.

According to this, since the difference information is generated, the difference between the degree of empathy indicated by the first degree-of-empathy information and the degree of empathy indicated by the second degree-of-empathy information can be presented or fed back to the first user, for example, after the end of online communication between the first user and the second user. As a result of that, the first user can analyze situations in the online communication in detail with reference to the difference in degree of empathy between the first degree-of-empathy information and the second degree-of-empathy information.

Further, in one general aspect, the techniques disclosed here feature an information processing method that is executed by one or more computers, the information processing method including: acquiring first biological information of a first user and second biological information of a second user; acquiring relationship information that indicates a relationship between the first user and the second user; determining, on the basis of the relationship information, whether the relationship between the first user and the second user is good; (i) in a case where it is determined that the relationship is good, outputting first degree-of-empathy information that is information generated on the basis of the first biological information and the second biological information and that indicates a degree of empathy between the first user and the second user; and (ii) in a case where it is determined that the relationship is not good, outputting second degree-of-empathy information that indicates a degree of empathy that is higher than the degree of empathy indicated by the first degree-of-empathy information.

According to this, for example, when online communication involving the use of one or more computers is being performed, information that indicates a degree of empathy between a first user and a second user of a plurality of participants in the online communication is outputted. The information is first degree-of-empathy information or second degree-of-empathy information. Accordingly, presenting the degree of empathy between the first user and the second user to the first user, i.e. feeding back the degree of empathy to the first user, allows the first user to properly grasp the state of the second user to facilitate communication.

Furthermore, when the first user does not have a good relationship with the second user (i.e. is in a state of poor relationship), a degree of empathy that is higher than an actual degree of empathy that is the degree of empathy indicated by the first degree-of-empathy information is fed back to the first user. On the other hand, feeding back the actual low degree of empathy to the first user when the first user is in the state of poor relationship may cause an increase in extent of bewilderment of the first user with respect to the second user in communication and make communication difficult. However, in the information processing method according to the aspect of the present disclosure, as mentioned above, when the first user is in the state of poor relationship, the degree of empathy that is higher than the actual degree of empathy is fed back to the first user. This suppresses the increase in extent of the state of stress of the first user, making it possible to more smoothly perform communication.

Further, in one general aspect, the techniques disclosed here feature an information processing system including: a first photodetector that detects first scattered light scattered inside a first user; a second photodetector that detects second scattered light scattered inside a second user; and a processing apparatus that generates, on the basis of temporal changes in intensity of the first scattered light, first biological data containing information on heartbeat of the first user and that generates, on the basis of temporal changes in intensity of the second scattered light, second biological data containing information on heartbeat of the second user. The processing apparatus analyzes a correlation between the heartbeat of the first user and the heartbeat of the second user on the basis of the first biological data and the second biological data. The processing apparatus derives a degree of empathy between the first user and the second user on the basis of the correlation thus analyzed. The processing apparatus determines, on the basis of the first biological data, whether the heartbeat of the first user is higher than or equal to a threshold. In a case where the heartbeat of the first user is lower than the threshold, the processing apparatus outputs, with use of a first algorithm, first empathy information that indicates the degree of empathy. In a case where the heartbeat of the first user is higher than or equal to the threshold, the processing apparatus outputs, with use of a second algorithm that is different from the first algorithm, second empathy information that indicates a higher degree of empathy than does the first empathy information. The first photodetector and the second photodetector may each, for example, be a wearable device including a phototransistor and a photodiode. Further, the first empathy information and the second empathy information may also be called "first degree-of-empathy information" and "second degree-of-empathy information", respectively, and the first biological data and the second biological data" may also be called "first biological information" and "second biological information", respectively.

The following describes embodiments in concrete terms with reference to the drawings.

It should be noted that the embodiments to be described below each illustrate a comprehensive and specific example. The numerical values, shapes, materials, constituent elements, placement and topology of constituent elements, steps, orders of steps, or other features that are shown in the following embodiments are just a few examples and are not intended to limit the present disclosure. Further, those of the constituent elements in the following embodiments which are not recited in an independent claim reciting the most superordinate concept are described as optional constituent elements.

Further, the drawings are schematic views and are not necessarily strict illustrations. Further, in the drawings, the same constituent elements are given the same reference signs.

Embodiment

FIG. 1 is a diagram showing a configuration of an information processing system according to the present embodiment.

An information processing system 1000 according to the present embodiment is, for example, a system for performing online communication and includes a server 100 and a plurality of terminal devices 200.

Each of the plurality of terminal devices 200 is a computer that is used by a user in performing online communication. Such a terminal device 200 is configured as a personal computer, a smartphone, a tablet terminal, or other devices. That is, the user uses the terminal device 200 to participate in online communication.

The user is also called a "participant in online communication". Further, in the present embodiment, the number of terminal devices 200 is 2, and online communication is performed between the two terminal devices 200; however, the number of terminal devices 200 is not limited to 2 but may be three or larger. Further, a first user, who is one of a plurality of participants in online communication, uses one of the plurality of terminal devices 200, and a second user, who is another participant, uses another one of the plurality of terminal devices 200.

The server 100 is a computer that is connected to the plurality of terminal devices 200 via a communication network Nt such as the Internet.

In such an information processing system 1000, each terminal device 200 sends the user's voice data to the server 100 via the communication network Nt in performing online communication. Upon receiving the voice data from the terminal device 200, the server 100 sends the voice data thus received to another user's terminal device 200 via the communication network Nt.

Although, in the information processing system 1000, voice data is sent and received as mentioned above, the user's video data (also called a "moving image") may be sent and received together with voice data. Further, either wired communication or wireless communication may be used as communication between the server 100 and the terminal devices 200.

Figure 2:
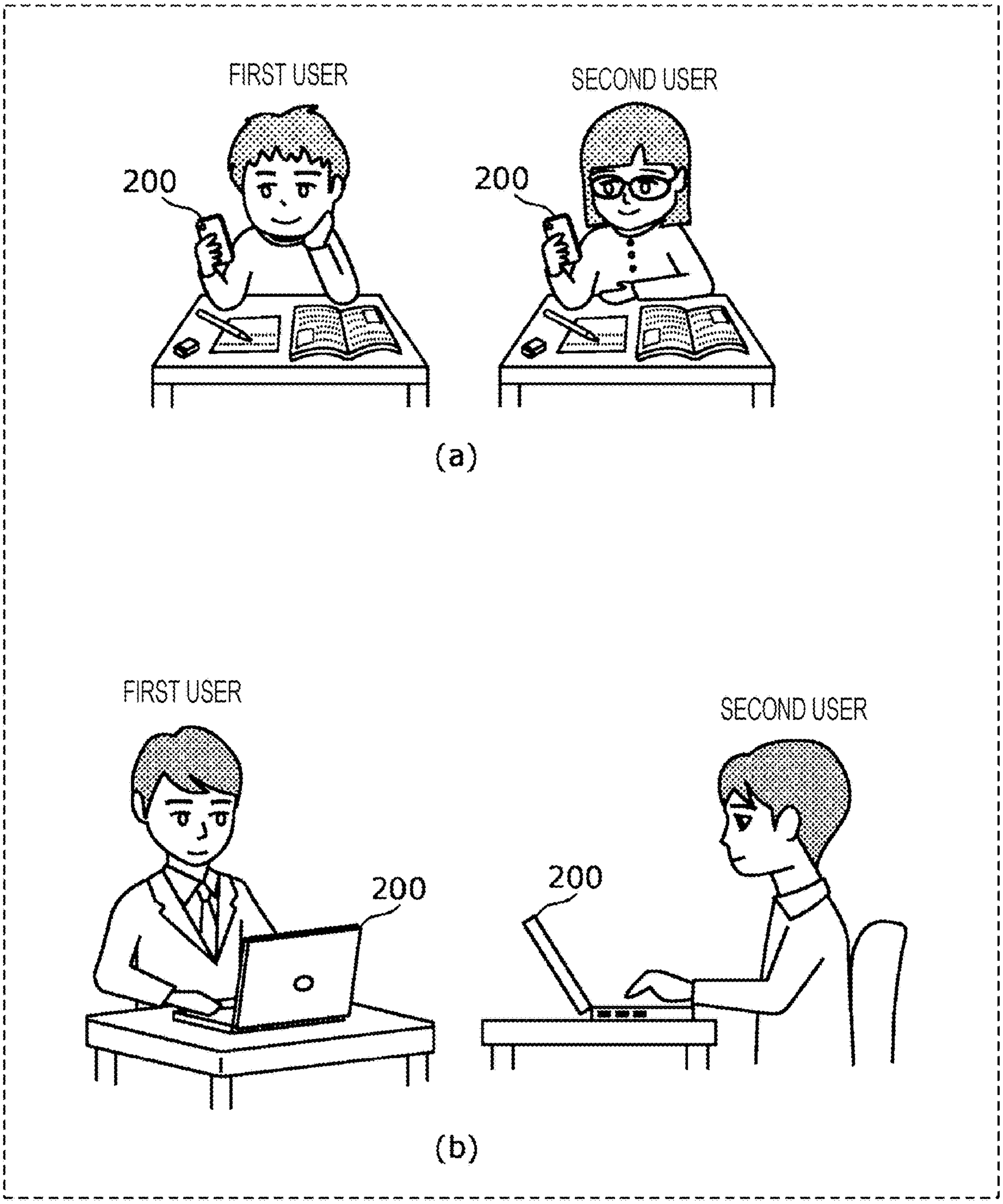
FIG. 2 illustrates diagrams each showing an example of a state where online communication according to the embodiment is being performed.

FIG. 2 illustrates diagrams each showing an example of a state where online communication is being performed.

For example, as shown in (a) of FIG. 2, the first user participates in the online communication with the use of a terminal device 200 configured as a smartphone. Also, the second user participates in the online communication with the use of a terminal device 200 configured as a smartphone. Moreover, the online communication is performed between the first user and the second user with the use of the information processing system 1000.

Further, as shown in (b) of FIG. 2, the first user participates in the online communication with the use of a terminal device 200 configured as a laptop personal computer. Also, the second user participates in the online communication with the use of a terminal device 200 configured as a smartphone. Moreover, the online communication is performed between the first user and the second user with the use of the information processing system 1000.

In the information processing system 1000 according to the present embodiment, a degree of empathy between the first user and the second user is presented from the terminal device 200 of the first user to the first user. Specifically, the degree of empathy is presented to the first user by being displayed on a display of the terminal device 200.

In the present embodiment, an example in which the degree of empathy is presented to the first user is described with reference to a processing operation of the terminal device 200 of the first user; however, also in a case where the degree of empathy is presented to the second user, a processing operation that is similar to that of the terminal device 200 of the first user is performed also in the terminal device 200 of the second user.

Figure 3:
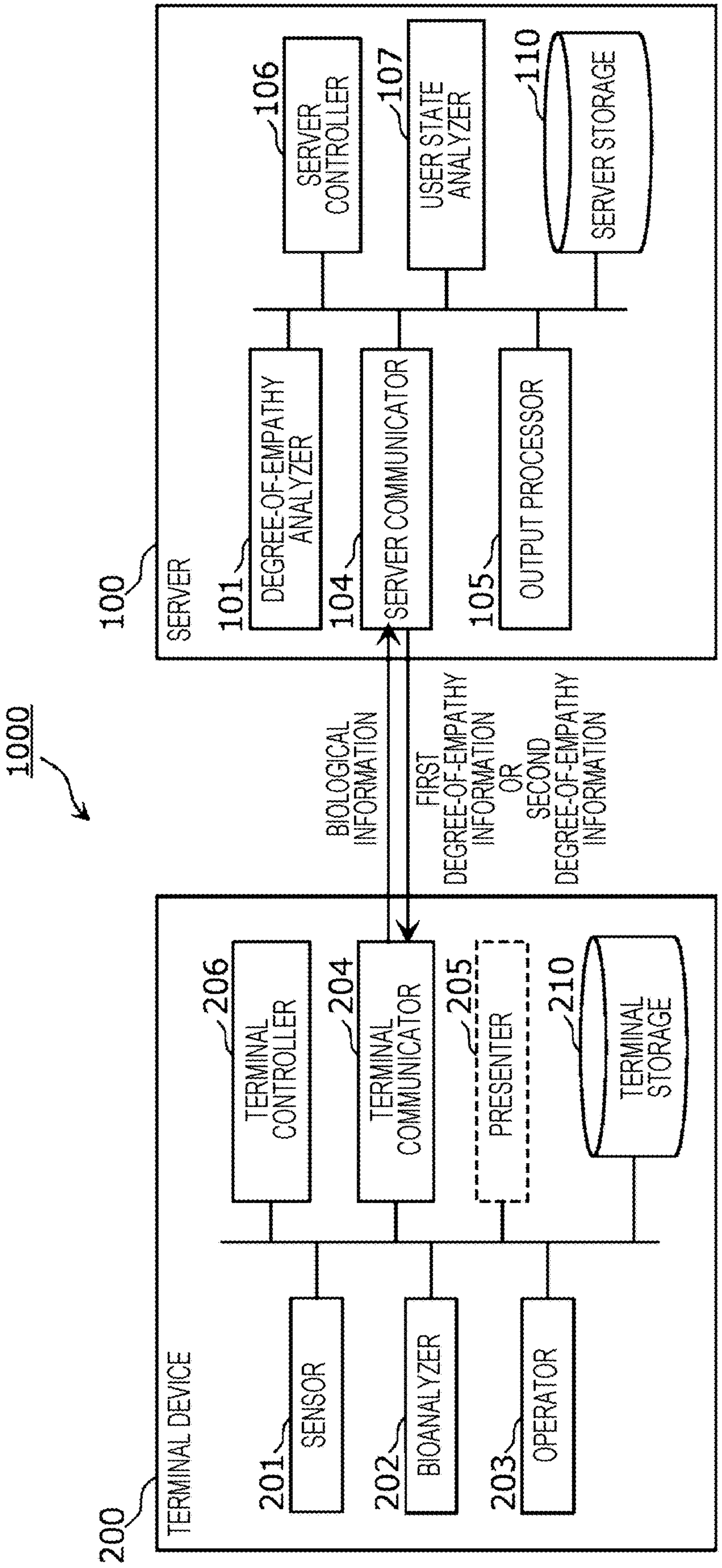
FIG. 3 is a block diagram showing examples of configurations of a server and each terminal device according to the embodiment.

FIG. 3 is a block diagram showing examples of configurations of the server 100 and each of the terminal devices 200 according to the present embodiment.

Each of the terminal devices 200 includes a sensor 201, a bioanalyzer 202, an operator 203, a terminal communicator 204, a presenter 205, a terminal controller 206, and a terminal storage 210.

The sensor 201 includes a camera that photographs the face of the user of the terminal device 200 and outputs, as sensing information, a captured image obtained by photographing. The captured image is a moving image. Furthermore, the sensor 201 includes, for example, a microphone that acquires the user's voice, converts the voice into voice data as an electrical signal, and outputs the voice data. The sensing information may contain the captured image and the voice data.

The bioanalyzer 202 acquires the sensing information from the sensor 201 and, by analyzing the sensing information, generates biological information serving as information on the user's living body. Moreover, the bioanalyzer 202 outputs the biological information. The biological information may, for example, be information (i.e. heartbeat information) on the user's heartbeat that is obtained from the captured image. Specifically, the biological information may be information that indicates a parameter such as a heart rate or a heartbeat fluctuation in chronological order. Further, the biological information may be information that indicates the user's facial expression in chronological order. For example, the facial expression is labeled or expressed by delight, anger, sorrow, pleasure, or other emotions.

Although, in the present embodiment, the bioanalyzer 202 is provided in the terminal device 200, the bioanalyzer 202 may be provided in the server 100. In this case, the sensing information that is outputted from the sensor 201 is sent from the terminal device 200 to the server 100. Further, biological information that is generated by the bioanalyzer 202 of the terminal device 200 that the first user uses is biological information of the first user and is also called "first biological information". Similarly, biological information that is generated by the bioanalyzer 202 of the terminal device 200 that the second user uses is biological information of the second user and is also called "second biological information".

The presenter 205 includes, for example, a display that displays an image and a loudspeaker that outputs a voice. Examples of the display include, but are not limited to, a liquid crystal display, a plasma display, and an organic EL (electroluminescence) display. Further, although, in the present embodiment, the presenter 205 is provided in the terminal device 200, the presenter 205 may be a device that is connected to the terminal device 200.

The operator 203 accepts an input operation carried out by the user and outputs, to the terminal controller 206, a signal that corresponds to the input operation. Such an operator 203 is configured, for example, as a keyboard, a touch sensor, a touchpad, a mouse, a microphone, or other devices. Further, the operator 203 may be combined with the presenter 205 into a touch panel. That is, the operator 203 is disposed in the display and, when the user touches an image, such as an icon, that is displayed on the display, accepts an input operation that corresponds to the image.

The terminal communicator 204 communicates with the server 100 via the communication network Nt. This communication may be wired communication or wireless communication.

The terminal storage 210 is a storage medium and, for example, has stored therein a user ID serving as the user's identification information, the after-mentioned relationship information, or other information. Such a storage medium may be a hard disk drive, a random-access memory (RAM), a read-only memory (ROM), or a semiconductor memory. Further, the storage medium may be volatile or nonvolatile.

The terminal controller 206 controls the sensor 201, the bioanalyzer 202, the terminal communicator 204, the presenter 205, and the terminal storage 210.

For example, the terminal controller 206 causes voice data that is outputted from the sensor 201 to be sent from the terminal communicator 204 to the server 100. Further, every time biological information is outputted from the bioanalyzer 202, the terminal controller 206 causes the biological information to be sent from the terminal communicator 204 to the server 100 via the communication network Nt. In sending such voice data and biological information, the terminal controller 206, for example, associates the user ID stored in the terminal storage 210 with the voice data and the biological information and causes the voice data and the biological information with which the user ID is associated to be sent from the terminal communicator 204.

Further, every time the terminal communicator 204 receives degree-of-empathy information sent from the server 100 via the communication network Nt, the terminal controller 206 causes the presenter 205 to present a degree of empathy indicated by the degree-of-empathy information. That is, under control of the terminal controller 206, the presenter 205 presents, to the user, the degree of empathy indicated by the degree-of-empathy information. For example, the presenter 205 presents the degree of empathy to the user by displaying the degree of empathy on the display. As will be mentioned later, the degree-of-empathy information includes first degree-of-empathy information and second degree-of-empathy information.

The server 100 includes a degree-of-empathy analyzer 101, a server communicator 104, an output processor 105, a server controller 106, a user state analyzer 107, and a server storage 110.

The server communicator 104 communicates with the terminal device 200 via the communication network Nt. This communication may be wired communication or wireless communication. The server communicator 104 is an example of an acquirer that acquires first biological information of a first user and second biological information of a second user. That is, the server communicator 104 receives biological information that is sent from each of the plurality of terminal devices 200 via the communication network Nt. A user ID is associated with this biological information. Accordingly, the server 100 can identify which participant the biological information belongs to. Further, the server communicator 104 sends, to the terminal device 200 via the communication network Nt, degree-of-empathy information that is outputted from the output processor 105.

The server storage 110 is, for example, a storage medium on which to store first degree-of-empathy information that indicates a degree of empathy derived by the degree-of-empathy analyzer 101 and second degree-of-empathy information that indicates a degree of empathy derived by the output processor 105. As noted above, such a storage medium is a hard disk drive, a RAM, a ROM, or a semiconductor memory. Further, the storage medium may be volatile or nonvolatile.

The degree-of-empathy analyzer 101 derives a degree of empathy between a plurality of users on the basis of biological information of the user of each of the plurality of terminal devices 200. Moreover, the degree-of-empathy analyzer 101 generates and outputs first degree-of-empathy information that indicates the degree of empathy. That is, the degree-of-empathy analyzer 101 derives a degree of empathy between the first user and the second user on the basis of the biological information of the first user and the second biological information of the second user received by the server communicator 104 and generates and outputs first degree-of-empathy information that indicates the degree of empathy.

A degree of empathy is an extent of empathy between a person and a person. The larger the extent of empathy is, the larger numerical value the degree of empathy assumes, and the smaller the extent of empathy is, the smaller numerical value the degree of empathy assumes. Further, empathy may, for example, be a state where a person and a person share their emotional states, mental states, psychosomatic states, or other states with each other. Alternatively, empathy may be a state where a person and a person approve of another person's remarks, action, or other behavior.

Specifically, for example, in a case where biological information of two participants indicates the same facial expression (e.g. delight) at the same timing, the degree-of-empathy analyzer 101 derives a high degree of empathy as a degree of empathy between the two participants. Information on heartbeat such as a heart rate and a heartbeat fluctuation reflects the inner state of a person and is suitable to deriving the degree of empathy. While the facial expression may reflect the inner state of a person, it also contains outward information such as a fake smile. Therefore, the degree-of-empathy analyzer 101 may derive the degree of empathy with the use of both the information on heartbeat and the facial expression. In this case, the biological information indicates, for example, the heart rate or the heart fluctuation and the facial expression in chronological order. For example, the degree-of-empathy analyzer 101 may derive a final degree of empathy by performing a linear combination of a degree of heartbeat empathy that is derived on the basis of the information on heartbeat and a degree of facial expression empathy that is derived on the basis of the facial expression. At this point in time, the degree of heartbeat empathy and the degree of facial expression empathy are subjected to weighted addition. Moreover, in a case where the information on heartbeat is acquired with a high degree of accuracy, the degree-of-empathy analyzer 101 assigns a greater weight to the degree of heartbeat empathy, and in a case where the information on heartbeat is not acquired with a high degree of accuracy, the degree-of-empathy analyzer 101 assigns a greater weight to the degree of facial expression empathy.

With biological information that is sent from a terminal device 200, a user ID is associated. Accordingly, for example, by using a user ID of the first user and a user ID of the second user, the degree-of-empathy analyzer 101 can identify the first biological information of the first user and the second biological information of the second user. Processing details of the degree-of-empathy analyzer 101 according to the present embodiment will be described in the end of the present embodiment.

The user state analyzer 107 analyzes and identifies the state of the user of each terminal device 200. For example, the user state analyzer 107 analyzes the state of the first user. More specifically, the user state analyzer 107 determines, on the basis of the first biological information, whether the first user is in a state of stress. In the present embodiment, the state of stress may be a state of tension or a state of depression. For example, if the biological information is information on heartbeat and in a case where there is a sharp rise in heart rate indicated by the information or in a case where the heart rate is continuously at a numerical value higher than or equal to a threshold for a certain period of time or longer, the user state analyzer 107 may determine that the first user is in the state of stress. Alternatively, in a case where the biological information indicates a facial expression and in a case where the facial expression indicated by the biological information is neither a delightful nor joyful facial expression, the user state analyzer 107 may determine that the first user is in the state of stress. Further, the user state analyzer 107 may determine, on the basis of sensing information of the first user, whether the first user is in a state of stress. For example, by performing a speech analysis process on voice data of the first user, the user state analyzer 107 may determine whether the first user is in a state of stress.

Furthermore, the user state analyzer 107 acquires, from the server storage 110, relationship information that indicates a relationship between the first user and the second user. Moreover, the user state analyzer 107 determines, on the basis of the relationship information, whether the relationship between the first user and the second user is good.

The relationship information is data obtained when communication was performed in the past between the first user and the second user. For example, the relationship information indicates, as the aforementioned relationship, at least one of the number, duration, frequency, and content of conversations between the first user and the second user. According to this, using the relationship information makes it possible to properly determine whether the relationship between the first user and the second user is good. In a specific example, in a case where the relationship information indicates the number of conversations and when the number of conversations is smaller than a threshold, the user state analyzer 107 determines that the relationship is not good, and when the number of conversations is larger than or equal to the threshold, the user state analyzer 107 determines that the relationship is good. This makes it possible to quantitatively properly determine whether the relationship between the first user and the second user is good. In the present embodiment, determining whether the relationship between the first user and the second user is good is not limited to determining that the first user and the second user actually have built a good relationship with each other.

This relationship information may indicate a degree of empathy between the first user and the second user that was derived in the past by the degree-of-empathy analyzer 101. If the degree of empathy is higher than or equal to a threshold, the user state analyzer 107 determines that the relationship between the first user and the second user is good. On the other hand, if the degree of empathy is lower than a threshold, the user state analyzer 107 determines that the relationship between the first user and the second user is not good.

Further, the relationship information may be voice data of the first user and the second user obtained when communication was performed in the past. The voice data is data that is obtained by the microphone of the sensor 201 of each terminal device 200. For example, by performing a voice analysis process, a natural language process, or other processes on the voice data, the user state analyzer 107 determines whether the communication of that time is positive or negative. In a specific example, if a predetermined word is contained in a conversation indicated by the voice data, it may be determined that the communication is positive, and if another predetermined word is contained, it may be determined that the communication is negative.

Moreover, if the user state analyzer 107 determines that the communication is positive, the user state analyzer 107 determines that the relationship between the first user and the second user is good. On the other hand, if the user state analyzer 107 determines that the communication is negative, the user state analyzer 107 determines that the relationship between the first user and the second user is not good.

Further, the relationship information may be facial expression data that represents facial expressions of the first user and the second user during communication performed in the past. The facial expression data is biological information generated by the bioanalyzer 202 of each terminal device 200. For example, the user state analyzer 107 identifies the number or duration of smiles represented by the facial expression data. Moreover, if the number or duration of smiles is larger than or equal to a threshold, the user state analyzer 107 determines that the relationship between the first user and the second user is good. On the other hand, if the number or duration of smiles is smaller than the threshold, the user state analyzer 107 determines that the relationship between the first user and the second user is not good.

Further, the relationship information may be information on the number of times or frequency at which communication was performed between the first user and the second user with a communication tool such as chat, e-mail, or a social networking service (SNS). For example, the relationship information may indicate, for example, the number of times data was sent and received for communication through e-mail or an SNS. If the number of times is larger than or equal to a threshold, the user state analyzer 107 determines that the relationship between the first user and the second user is good. On the other hand, if the number of times is smaller than the threshold, the user state analyzer 107 determines that the relationship between the first user and the second user is not good.

Moreover, the user state analyzer 107 generates and outputs user state information that indicates the state of the first user thus determined. The user state information indicates whether the first user is in a state of stress and indicates whether the relationship between the first user and the second user is good. A state where the first user does not have a good relationship with the second user is hereinafter also called a "state of poor relationship". Accordingly, the aforementioned user state information indicates whether the first user is in a state of stress and whether the first user in a state of poor relationship.

When the user state analyzer 107 determines that the first user is in the state of stress, the user state analyzer 107 may further derive the extent of the state of stress as a degree of stress. Similarly, when the user state analyzer 107 determines that the first user is in the state of poor relationship, the user state analyzer 107 may derive the extent of poor relationship as a degree of poor relationship. For example, the degree of poor relationship takes on a larger value when the aforementioned number of conversations is smaller. Moreover, the user state analyzer 107 may derive a degree of stress and poor relationship, for example, by adding up the degree of stress and the degree of poor relationship. The degree of stress, the degree of poor relationship, and the degree of stress and poor relationship each indicate the extent of difficulty the first user has communicating with the second user, and is also called a "degree of communication difficulty". As will be mentioned later, such a degree of communication difficulty may be reflected in the magnitude of a correction value for the degree of empathy.

Although, in the present embodiment, the user state analyzer 107 is provided in the server 100, the user state analyzer 107 may be provided in the terminal device 200. In this case, the user state analyzer 107 may use relationship information stored in the terminal storage 210.

Further, processing details of the identification of a state of stress by the user state analyzer 107 will be described in the end of the present embodiment, together with the processing details of the degree-of-empathy analyzer 101.

The output processor 105 acquires first degree-of-empathy information that is outputted from the degree-of-empathy analyzer 101 and further acquires, from the user state analyzer 107, user state information that indicates the state of the first user. Moreover, the output processor 105 determines, on the basis of the state of the first user indicated by the user state information, whether to correct the degree of empathy indicated by the first degree-of-empathy information.

Specifically, in a case where the user state information indicates that the first user is not in the state of stress and not in the state of poor relationship, the output processor 105 determines not to correct the degree of empathy. As a result of that, the output processor 105 outputs the first degree-of-empathy information thus acquired as-is. On the other hand, in a case where the user state information indicates that the first user is in at least one of the state of stress and the state of poor relationship, the output processor 105 determines to correct the degree of empathy. As a result of that, the output processor 105 corrects the first degree-of-empathy information thus acquired. Specifically, the output processor 105 corrects the degree of empathy so that the degree of empathy becomes higher. Moreover, the output processor 105 generates and outputs second degree-of-empathy that indicates the degree of empathy thus corrected. The first degree-of-empathy information and the second degree-of-empathy information thus outputted from the output processor 105 are sent from the server communicator 104 to the terminal device 200.

Thus, in a case where it is determined that the first user is not in the state of stress, the output processor 105 according to the present embodiment outputs first degree-of-empathy information that is information generated on the basis of the first biological information and the second biological information and that indicates a degree of empathy between the first user and the second user. Further, in a case where it is determined that the first user is in the state of stress, the output processor 105 outputs second degree-of-empathy information that indicates a degree of empathy that is higher than the degree of empathy indicated by the first degree-of-empathy information. Further, the output processor 105 outputs the second degree-of-empathy information in a case where it is determined that the first user is in the state of stress and does not have a good relationship. Alternatively, in a case where it is determined that the relationship between the first user and the second user is good, the output processor 105 outputs first degree-of-empathy information that is information generated on the basis of the first biological information and the second biological information and that indicates a degree of empathy between the first user and the second user. Moreover, in a case where it is determined that the relationship is not good, the output processor 105 outputs second degree-of-empathy information that indicates a degree of empathy that is higher than the degree of empathy indicated by the first degree-of-empathy information.

Although, in the present embodiment, the output processor 105 is provided in the server 100, the output processor 105 may be provided in the terminal device 200. In this case, first degree-of-empathy information generated by the degree-of-empathy analyzer 101 and user state information generated by the user state analyzer 107 are sent from the server 100 to the terminal device 200.

The server controller 106 controls the degree-of-empathy analyzer 101, the server communicator 104, the output processor 105, the user state analyzer 107, and the server storage 110. For example, every time biological information is received by the server communicator 104, the server controller 106 causes the degree-of-empathy analyzer 101 to execute a process based on the biological information. Further, every time first degree-of-empathy information or second degree-of-empathy information is outputted by the output processor 105, the server controller 106 causes the server communicator 104 to send those pieces of degree-of-empathy information to the terminal device 200. Furthermore, when the server communicator 104 receives voice data from the terminal device 200, the server controller 106 causes the voice data to be sent from the server communicator 104 to another terminal device 200. The loudspeaker of the presenter 205 of the terminal device 200 outputs a voice represented by the voice data. Sending and receiving such voice data causes communication to be performed between participants.

Figure 4:
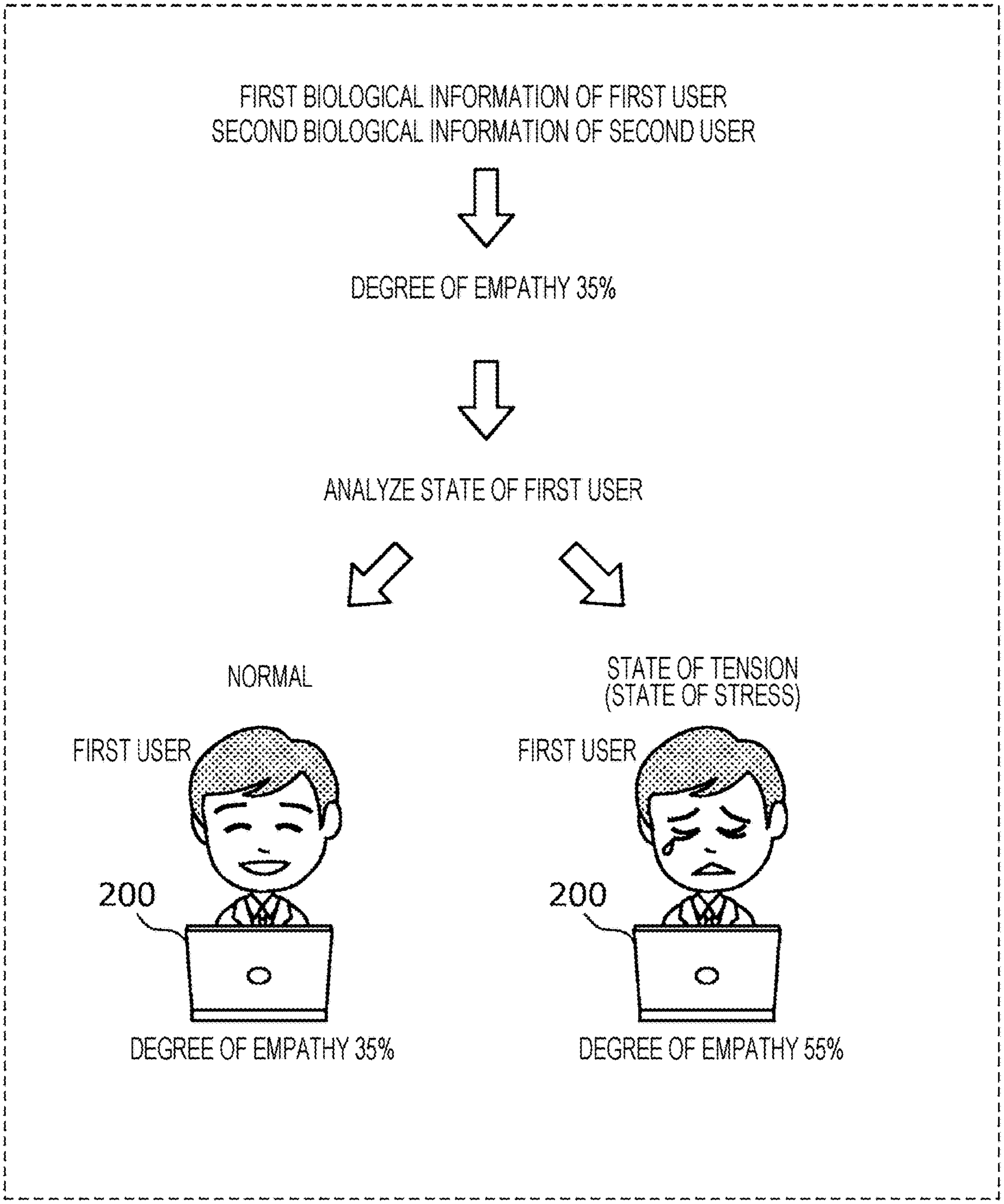
FIG. 4 is a diagram showing an example of a process up to presentation of a degree of empathy according to the embodiment.

FIG. 4 is a diagram showing an example of a process up to presentation of a degree of empathy according to the present embodiment.

First, the degree-of-empathy analyzer 101 of the server 100 derives a degree of empathy between the first user and the second user with the use of the first biological information of the first user and the second biological information of the second user sent from the two terminal devices 200 to the server 100. For example, the degree-of-empathy analyzer 101 derives 35% as the degree of empathy. The degree-of-empathy analyzer 101 outputs, as first degree-of-empathy information, information that indicates such a degree of empathy.

The user state analyzer 107 analyzes the state of the first user on the basis of the first biological information of the first user. For example, the user state analyzer 107 determines whether the first user is in a state of stress such as a state of tension.

The output processor 105 corrects the degree of empathy derived by the degree-of-empathy analyzer 101, i.e. the degree of empathy indicated by the first degree-of-empathy information, according to a result of the analysis of the state of the first user by the user state analyzer 107. For example, when it is determined by the analysis conducted by the user state analyzer 107 that the first user is in a normal state, i.e. not in the state of tension, the output processor 105 determines not to correct the degree of empathy. As a result of that, the output processor 105 outputs the first degree-of-empathy information without correcting the degree of empathy indicated by the first degree-of-empathy information.

On the other hand, when it is determined by the analysis conducted by the user state analyzer 107 that the first user is in the state of tension, the output processor 105 determines to correct the degree of empathy. As a result of that, the output processor 105 corrects the degree of empathy indicated by the first degree-of-empathy information. For example, the output processor 105 corrects the degree of empathy "35%" indicated by the first degree-of-empathy information so that it becomes "55%". Moreover, the output processor 105 generates and outputs second degree-of-empathy information that indicates the degree of empathy "55%" thus corrected. The first degree-of-empathy information of the second degree-of-empathy information thus outputted is sent to the terminal device 200 of the first user and displayed on the presenter 205 of the terminal device 200. That is, the degree of empathy "35%" or "55%" is presented to the first user. In other words, the degree of empathy is fed back to the first user.

For example, if a low degree of empathy is fed back to the first user in a case where the first user is in a state of stress, the first user is mentally shocked that the first user him/herself is not empathized with by the second user. This may result in a deterioration in mental state of the first user and lead to a further increase in extent of the state of stress. An increase in extent of the state of stress can make normal or smooth communication even more difficult.

To address this problem, the present embodiment is configured such that when the first user in the state of stress, a degree of empathy corrected to a value that is larger than an actual degree of empathy is fed back to the first user. This results in giving a mental feeling of security to the first user, making it possible to remedy the state of stress. Remedying the state of stress allows the first user to normally communicate, making it possible to achieve smooth online communication.

FIG. 4 shows an example of correction and presentation of a degree of empathy based on a state of stress; however, in the present embodiment, correction and presentation of a degree of empathy based on the relationship between the first user and the second user are performed in a manner similar to the example shown in FIG. 4.

For example, in the case of a poor human relationship such as the relationship between the first user and the second user, it is difficult for the users to communicate with each other in the first place. A low degree of empathy presented in such a case bewilders the first user to make it even more difficult for the first user to communicate.

To address this problem, the present embodiment is configured such that on the basis of the relationship between the first user and the second user as well as the state of stress of the first user, a degree of empathy that is higher than a degree of empathy (i.e. an actual degree of empathy or a measured result) derived by the degree-of-empathy analyzer 101 is derived and presented. That is, even if the first user is not in the state of stress, a degree of empathy that is higher than a measured result is derived and presented to the first user in a case where the relationship between the first user and the second user is not good. This results in giving a mental feeling of security to the first user, making it possible to remedy the bewildered state of the first user. Remedying the bewildered state allows the first user to normally communicate, making it possible to achieve smooth online communication.

Figure 5:
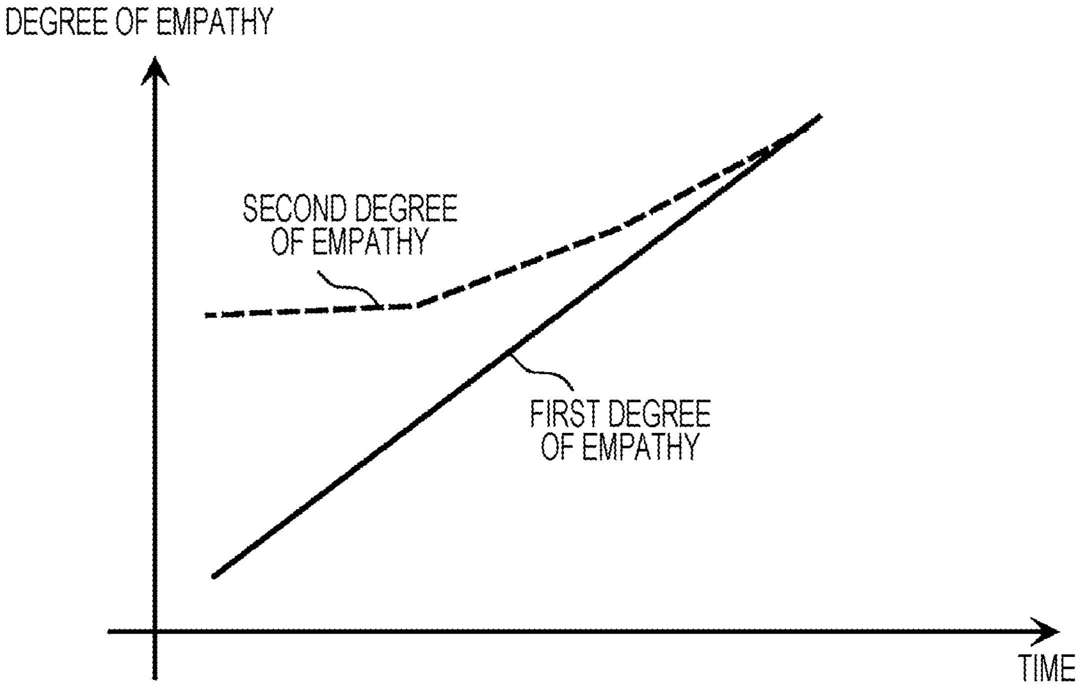
FIG. 5 is a diagram showing examples of temporal changes in a first degree of empathy and a second degree of empathy according to the embodiment.

FIG. 5 is a diagram showing examples of temporal changes in a first degree of empathy and a second degree of empathy. The first degree of empathy is an uncorrected degree of empathy (i.e. an actual degree of empathy) indicated by the first degree-of-empathy information, and the second degree of empathy is a corrected degree of empathy indicated by the second degree-of-empathy information.

The degree-of-empathy analyzer 101 periodically derives the first degree of empathy, which is a degree of empathy between the first user and the second user, on the basis of the latest first biological information of the first user and the latest second biological information of the second user. As a result of that, for example, as shown in FIG. 5, the degree-of-empathy analyzer 101 derives the first degree of empathy, which monotonically increases over time.

For example, as shown in FIG. 5, in a case where the output processor 105 corrects the first degree of empathy, the output processor 105 may derive the second degree of empathy by adding a larger correction value to the first degree of empathy when the first degree of empathy is lower. The correction value is a positive value. Alternatively, the output processor 105 may derive, as the second degree of empathy, a predetermined value or a value obtained by adding a random number to the value. The random number may be a numerical value that varies over time within the range of several percent of the predetermined value. Alternatively, the output processor 105 may derive, as the second degree of empathy, a random number that varies over time within a stipulated range.

Further, in deriving the second degree of empathy as mentioned above, the output processor 105 may clip the second degree of empathy to an upper limit in a case where the second degree of empathy exceeds the upper limit. For example, in a case where the first degree of empathy and the second degree of empathy are each expressed by a numerical value of 0 to 100 or in percentage, the aforementioned upper limit is 100. In a case where a value obtained by adding a correction value to the first degree of empathy exceeds the upper limit "100", the output processor 105 derives the upper limit "100" as the second degree of empathy.

In a case where a degree of communication difficulty is derived as mentioned above, the output processor 105 may derive the second degree of empathy by adding, to the first degree of empathy, a correction value that corresponds to the degree of communication difficulty. That is, the higher the degree of communication difficulty is, the larger correction value the output processor 105 may add to the first degree of empathy, and on the other hand, the lower the degree of communication difficulty is, the smaller correction value the output processor 105 may add to the first degree of empathy.

On the other hand, in a case where the first user is not in the state of stress and not in the state of poor relationship, the output processor 105 outputs the first degree-of-empathy information, which indicates the first degree of empathy, without correcting the first degree of empathy.

Thus, in the present embodiment, the degree-of-empathy analyzer 101 generates first degree-of-empathy information with the use of a first algorithm, and the output processor 105 generates second degree-of-empathy information with the use of a second algorithm that is different from the first algorithm. The first algorithm is, for example, a method for derivation of a degree of empathy based on biological information of each user. Further, in a specific example of generation of the second degree-of-empathy information, the output processor 105 generates the second degree-of-empathy information in accordance with the second algorithm by which a positive numerical value is added to the degree of empathy indicated by the first degree-of-empathy information. This positive numerical value is, for example, the aforementioned correction value. This makes it possible to properly make the degree of empathy indicated by the second degree-of-empathy information higher than the degree of empathy indicated by the first degree-of-empathy information and feed back the degree of empathy indicated by the second degree-of-empathy information to the first user.

Figure 6:
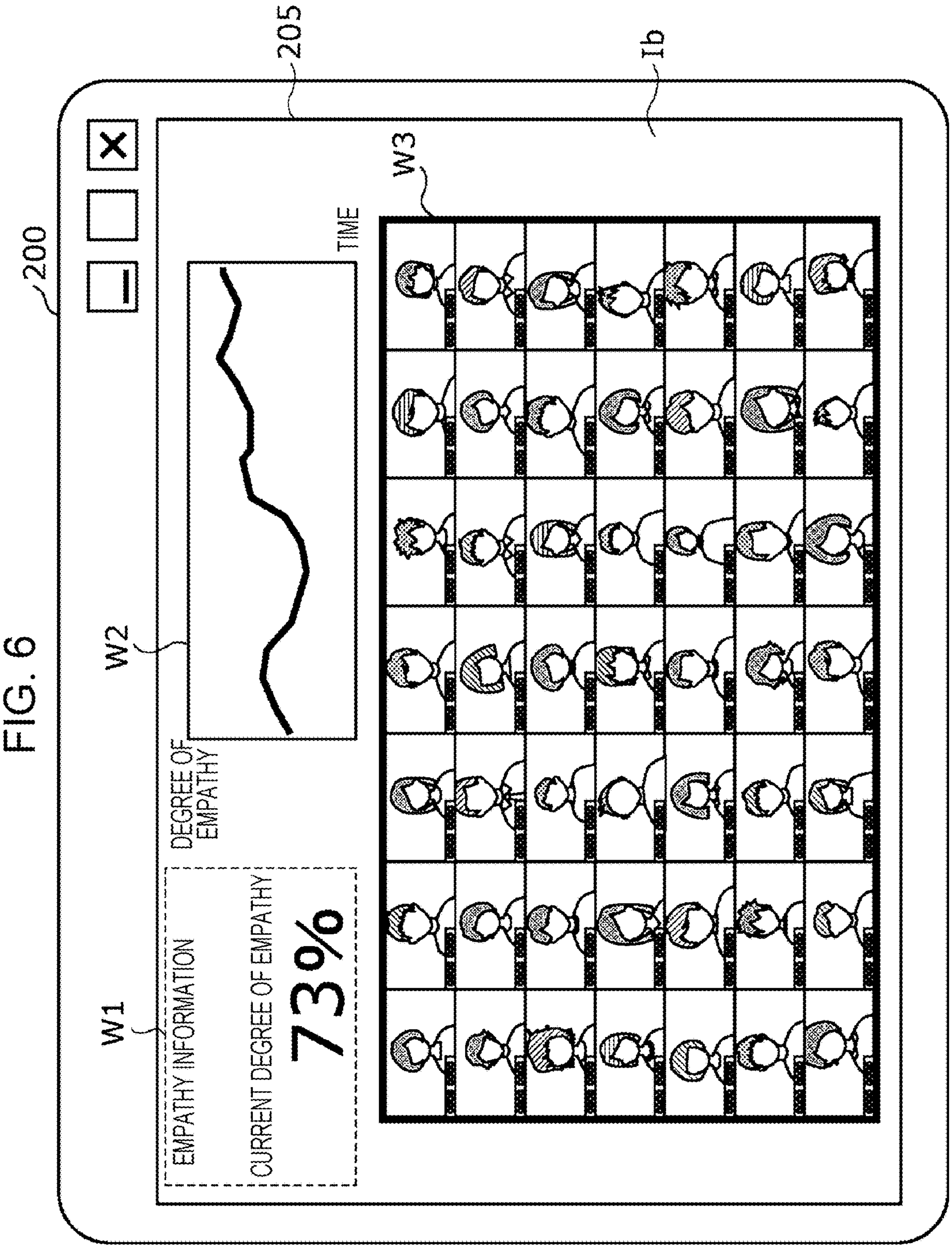
FIG. 6 is a diagram showing an example of presentation of a degree of empathy according to the embodiment.

FIG. 6 is a diagram showing an example of presentation of a degree of empathy according to the present embodiment.

When the terminal communicator 204 receives degree-of-empathy information sent from the server 100, the presenter 205 of the terminal device 200 displays, under control of the terminal controller 206, a degree of empathy indicated by the degree-of-empathy information. In a specific example, as shown in FIG. 6, the presenter 205 displays a display screen image Ib containing a degree-of-empathy area W1, a degree-of-empathy graph W2, and a moving image area W3. In the degree-of-empathy area W1, the current degree of empathy is expressed, for example, in percentage. The degree-of-empathy graph W2 is a graph that shows temporal changes in degree of empathy and, for example, has a horizontal axis representing time and a vertical axis representing the degree of empathy. In the moving image area W3, a moving image of each participant in online communication is displayed.

In the example shown in FIG. 6, a moving image of a participant obtained by photographing by a camera included in the sensor 201 of a terminal device 200 is sent from the terminal device 200 to the server 100. Furthermore, since a large number of participants are participating in the online communication with the use of their respective terminal devices 200, moving images of a large number of participants are being displayed in the moving image areas W3 of the presenters 205 of those terminal devices 200.

Thus, in the present embodiment, a degree of empathy is displayed on the presenter 205 of a terminal device 200. This degree of empathy is either a first degree of empathy or a second degree of empathy but is displayed without distinction therebetween. That is, even by looking at the degree of empathy displayed on the presenter 205, the first user cannot grasp whether the degree of empathy is a corrected one or an uncorrected, actually measured degree of empathy. Accordingly, regardless of whether the first user is in a state of stress or a state of poor relationship, a low degree of empathy is not presented to the first user. That is, a degree of empathy that is higher than the actual degree of empathy is presented to the first user as if it were the actual degree of empathy. This gives a feeling of security, making it possible to induce a positive mental state.

Thus, in the server 100 according to the present embodiment, the server communicator 104 acquires first biological information of a first user and second biological information of a second user, and the user state analyzer 107 determines, on the basis of the first biological information, whether the first user is in a state of stress. Moreover, (i) in a case where it is determined that the first user is not in the state of stress, the output processor 105 outputs first degree-of-empathy information that is information generated on the basis of the first biological information and the second biological information and that indicates a degree of empathy between the first user and the second user, and (ii) in a case where it is determined that the first user is in the state of stress, the output processor 105 outputs second degree-of-empathy information that indicates a degree of empathy that is higher than the degree of empathy indicated by the first degree-of-empathy information.

According to this, for example, when online communication involving the use of one or more computers is being performed, information that indicates a degree of empathy between a first user and a second user of a plurality of participants in the online communication is outputted. The information is first degree-of-empathy information or second degree-of-empathy information. Accordingly, presenting the degree of empathy between the first user and the second user to the first user, i.e. feeding back the degree of empathy to the first user, allows the first user to properly grasp the state of the second user to facilitate communication.

Furthermore, when the first user is in the state of stress, a degree of empathy that is higher than an actual degree of empathy that is the degree of empathy indicated by the first degree-of-empathy information is fed back to the first user. On the other hand, feeding back the actual low degree of empathy to the first user when the first user is in the state of stress may cause an increase in extent of the state of stress of the first user and make communication difficult. However, in the present embodiment, as mentioned above, when the first user is in the state of stress, the degree of empathy that is higher than the actual degree of empathy is fed back to the first user. This suppresses the increase in extent of the state of stress of the first user, making it possible to more smoothly perform communication.

Further, in the server 100 according to the present embodiment, the user state analyzer 107 acquires relationship information that indicates a relationship between the first user and the second user and determines, on the basis of the relationship information, whether the relationship between the first user and the second user is good. Moreover, the output processor 105 outputs the second degree-of-empathy information in a case where it is determined that the first user is in the state of stress and it is determined that the relationship is not good.

According to this, when the first user is in the state of stress and does not have a good relationship with the second user (i.e. is in a state of poor relationship), a degree of empathy that is higher than an actual degree of empathy that is the degree of empathy indicated by the first degree-of-empathy information is fed back to the first user. On the other hand, feeding back the actual low degree of empathy to the first user when the first user is in the state of poor relationship may cause an increase in extent of bewilderment of the first user with respect to the second user and make communication difficult. However, in the present embodiment, as mentioned above, when the first user is in the state of stress and the state of poor relationship, the degree of empathy that is higher than the actual degree of empathy is fed back to the first user. This suppresses the increases in extent of the state of stress and extent of bewilderment of the first user, making it possible to more smoothly perform communication.

Further, in the server 100 according to the present embodiment, the server communicator 104 acquires first biological information of a first user and second biological information of a second user, and the user state analyzer 107 acquires relationship information that indicates a relationship between the first user and the second user, and determines, on the basis of the relationship information, whether the relationship between the first user and the second user is good. Moreover, (i) in a case where it is determined that the relationship is good, the output processor 105 outputs first degree-of-empathy information that is information generated on the basis of the first biological information and the second biological information and that indicates a degree of empathy between the first user and the second user, and (ii) in a case where it is determined that the relationship is not good, the output processor 105 outputs second degree-of-empathy information that indicates a degree of empathy that is higher than the degree of empathy indicated by the first degree-of-empathy information.

Even in this case, as mentioned above, feeding back the degree of empathy to the first user allows the first user to properly grasp the state of the second user to facilitate communication. Furthermore, when the first user does not have a good relationship with the second user (i.e. is in a state of poor relationship), a degree of empathy that is higher than an actual degree of empathy that is the degree of empathy indicated by the first degree-of-empathy information is fed back to the first user. On the other hand, feeding back the actual low degree of empathy to the first user when the first user is in the state of poor relationship may cause an increase in extent of bewilderment of the first user with respect to the second user in communication and make communication difficult. However, in the present embodiment, as mentioned above, when the first user is in the state of poor relationship, the degree of empathy that is higher than the actual degree of empathy is fed back to the first user. This suppresses the increase in extent of the state of stress of the first user, making it possible to more smoothly perform communication.

Whether to correct the degree of empathy (i.e. the first degree of empathy) may be determined in advance by the first user. For example, the terminal controller 206 of the terminal device 200 that is used by the first user may cause the display of the presenter 205 to display a graphic image that prompts the first user to select whether to perform a process of correcting the degree of empathy. Such a graphic image is used as a GUI (graphical user interface). This allows the first user to, by carrying out an input operation on the operator 203 of the terminal device 200 in accordance with the graphic image being displayed on the presenter 205, switch between the process of correcting the degree of empathy and a process of not correcting the degree of empathy. The process of correcting the degree of empathy is also called a "degree-of-empathy correcting process", and the process of not correcting the degree of empathy is also called a "degree-of-empathy non-correcting process".

Specifically, a signal that corresponds to the input operation carried out by the first user is sent from the terminal communicator 204 of the terminal device 200 to the server 100. In a case where the signal represents switching to the degree-of-empathy correcting process, the server controller 106 of the server 100 causes the output processor 105 to execute the aforementioned correction according to the state of the first user. On the other hand, in a case where the signal represents switching to the degree-of-empathy non-correcting process, the server controller 106 does not cause the output processor 105 to execute the aforementioned correction according to the state of the first user. That is, regardless of what state the first user is in, the output processor 105 outputs the first degree-of-empathy information, which indicates the first degree of empathy, without correcting the first degree of empathy.

Further, although, in the aforementioned example, the first user switches between the processes on the degree of empathy that is presented to the first user, another user, e.g. the second user, may switch between the processes on the degree of empathy that is presented to the first user. For example, the terminal controller 206 of the terminal device 200 of the second user causes the display of the presenter 205 to display the aforementioned graphic image and a graphic image for selecting a user who is subjected to switching between the processes on the degree of empathy. The second user performs an input operation on the operator 203 in accordance with those graphic images. In accordance with the input operation, the terminal controller 206 causes a signal representing switching between the processes on the degree of empathy that is presented to the first user to be sent from the terminal communicator 204 to the server 100. As a result of that, in a case where the signal represents switching to the degree-of-empathy correcting process on the degree of empathy that is presented to the first user, the server controller 106 of the server 100 causes the output processor 105 to execute the aforementioned correction according to the state of the first user. On the other hand, in a case where the signal represents switching to the degree-of-empathy non-correcting process on the degree of empathy that is presented to the first user, the server controller 106 does not cause the output processor 105 to execute the aforementioned correction according to the state of the first user.

A participant other than the second user who participates in the online communication may use his/her terminal device 200 to switch between the processes on the degree of empathy that is presented to the first user. Alternatively, a user who are not participating in the online communication may use his/her terminal device 200 to switch between the processes on the degree of empathy that is presented to the first user.

Figure 7:
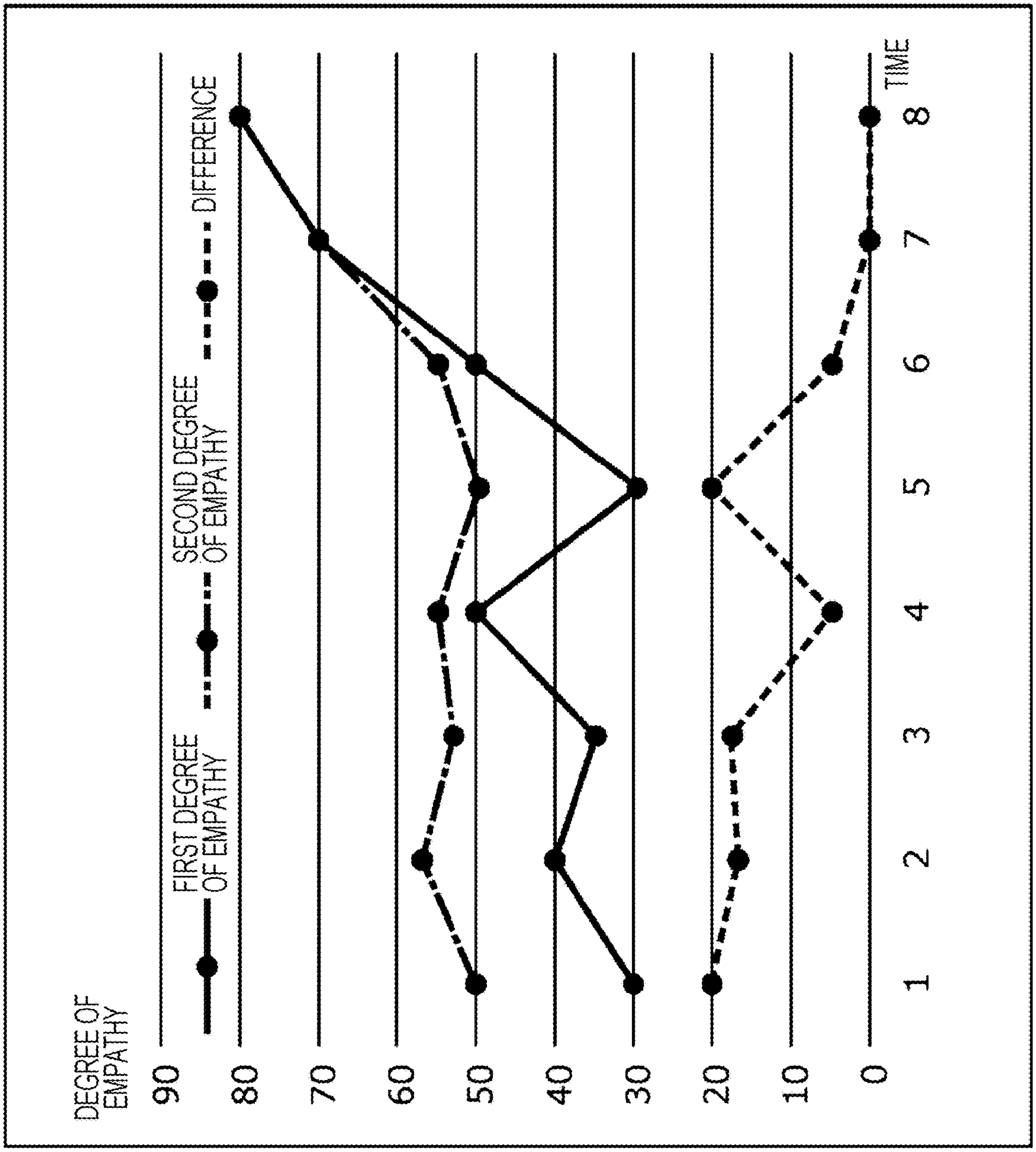
FIG. 7 is a diagram showing a first degree of empathy, a second degree of empathy, and a difference between the first degree of empathy and the second degree of empathy in chronological order according to the embodiment.

FIG. 7 is a diagram showing a first degree of empathy, a second degree of empathy, and a difference between the first degree of empathy and the second degree of empathy in chronological order.

Every time the first degree of empathy is derived by the degree-of-empathy analyzer 101, the server controller 106 of the server 100 stores, in the server storage 110, first degree-of-empathy information that indicates the first degree of empathy. Furthermore, every time the second degree of empathy is derived by the output processor 105, the server controller 106 stores, in the server storage 110, second degree-of-empathy information that indicates the second degree of empathy.

Furthermore, the server controller 106 may read out the first degree-of-empathy information and the second degree-of-empathy information from the server storage 110 and, as shown in FIG. 7, calculate the difference between the first degree of empathy and the second degree of empathy at each point in time. Moreover, the server controller 106 may cause history information that indicates the difference between the first degree of empathy and the second degree of empathy in chronological order to be sent from the server communicator 104 to the terminal device 200 of the first user. When the terminal communicator 204 receives the history information, the terminal controller 206 of the terminal device 200 of the first user may cause the presenter 205 to display the first degree of empathy, the second degree of empathy, and the difference, which are shown in chronological order by the history information.

This makes it possible to, even in a case where only the second degree of empathy is presented to the first user, subsequently feedback the first degree of empathy, which is an actual degree of empathy, and the difference to the first user.

Thus, in the present embodiment, the server controller 106 stores the first degree-of-empathy information and the second degree-of-empathy information in the server storage 110 and generates difference information that indicates a difference between the degree of empathy indicated by the first degree-of-empathy information stored in the server storage 110 and the degree of empathy indicated by the second degree-of-empathy information stored in the server storage 110. As with the aforementioned history information, the difference information may indicate the first degree of empathy and the second degree of empathy as well as the difference. Moreover, the difference information or the history information may be stored in the server storage 110. This makes it possible, for example, to, after the end of online communication between the first user and the second user, present or feed back the difference between the degree of empathy indicated by the first degree-of-empathy information and the degree of empathy indicated by the second degree-of-empathy information to the first user. As a result of that, the first user can analyze situations in the online communication in detail with reference to the difference in degree of empathy between the first degree-of-empathy information and the second degree-of-empathy information.

Figure 8A:
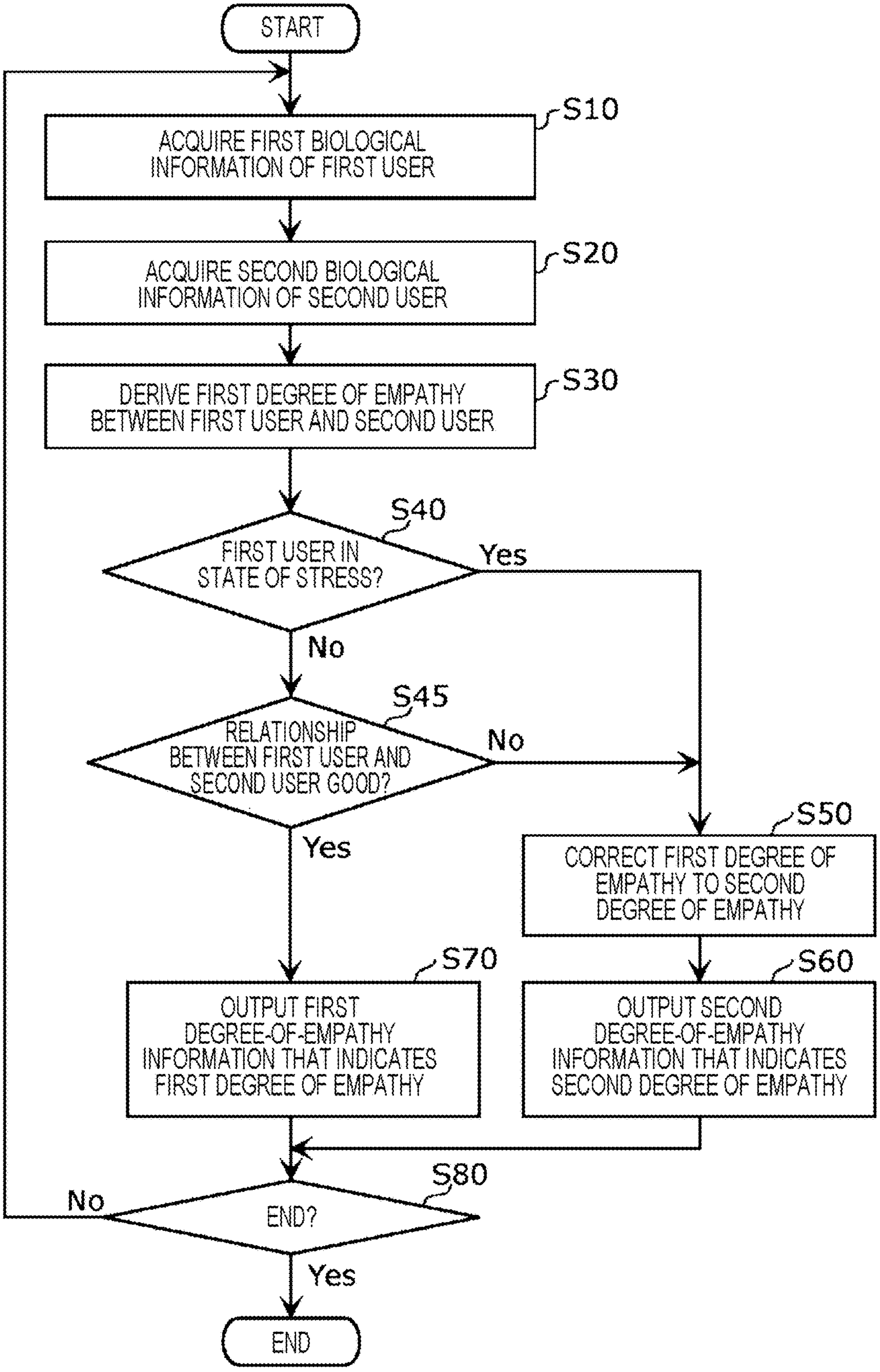
FIG. 8A is a flow chart showing an example of a processing operation of the server according to the embodiment.

FIG. 8A is a flow chart showing an example of a processing operation of the server 100 according to the present embodiment.

First, the server communicator 104 of the server 100 acquires first biological information of a first user from a terminal device 200 of the first user (step S10). Furthermore, the server communicator 104 acquires second biological information of a second user from a terminal device 200 of the second user (step S20).

The degree-of-empathy analyzer 101 outputs a degree of empathy between the first user and the second user as a first degree of empathy on the basis of the first biological information acquired in step S10 and the second biological information acquired in step S20 (step S30). After that, the degree-of-empathy analyzer 101 generates and outputs first degree-of-empathy information that indicates the first degree of empathy.

Next, the user state analyzer 107 determines, on the basis of the first biological information acquired in step S10, whether the first user is in a state of stress (step S40). When the user state analyzer 107 determines in step S40 that the first user is not in the state of stress (No in step S40), the user state analyzer 107 further determines whether a relationship between the first user and the second user is good (step S45).

Then, the output processor 105 acquires the first degree-of-empathy information outputted from the degree-of-empathy analyzer 101. When it is determined in step S40 that the first user is in the state of stress (Yes in step S40) or it is determined in step S45 that the relationship between the first user and the second user is not good (No in step S45), the output processor 105 corrects the first degree of empathy. That is, the output processor 105 corrects the first degree of empathy indicated by the first degree-of-empathy information to a second degree of empathy that is higher than the first degree of empathy (step S50). Then, the output processor 105 generates and outputs second degree-of-empathy information that indicates the second degree of empathy (step S60).

On the other hand, when it is determined in step S45 that the relationship between the first user and the second user is good (Yes in step S45), the output processor 105 outputs the first degree-of-empathy information without correcting the first degree of empathy indicated by the first degree-of-empathy information (step S70).

After step S70, the server controller 106 determines whether to end the process of online communication (step S80). When the server controller 106 determines that the process of online communication should not end (No in step S80), the server controller 106 causes each constituent element of the server 100 to execute the process from step S10. On the other hand, when the server controller 106 determines that the process of online communication should end (Yes in step S80), the server controller 106 ends the process of online communication.

Although, in the aforementioned example, the processing operation of the server 100 includes the process in steps S40 and S45, either of these steps does not need to be executed. For example, as shown in FIG. 8B, the process in step S45 does not need to be executed.

Figure 8B:
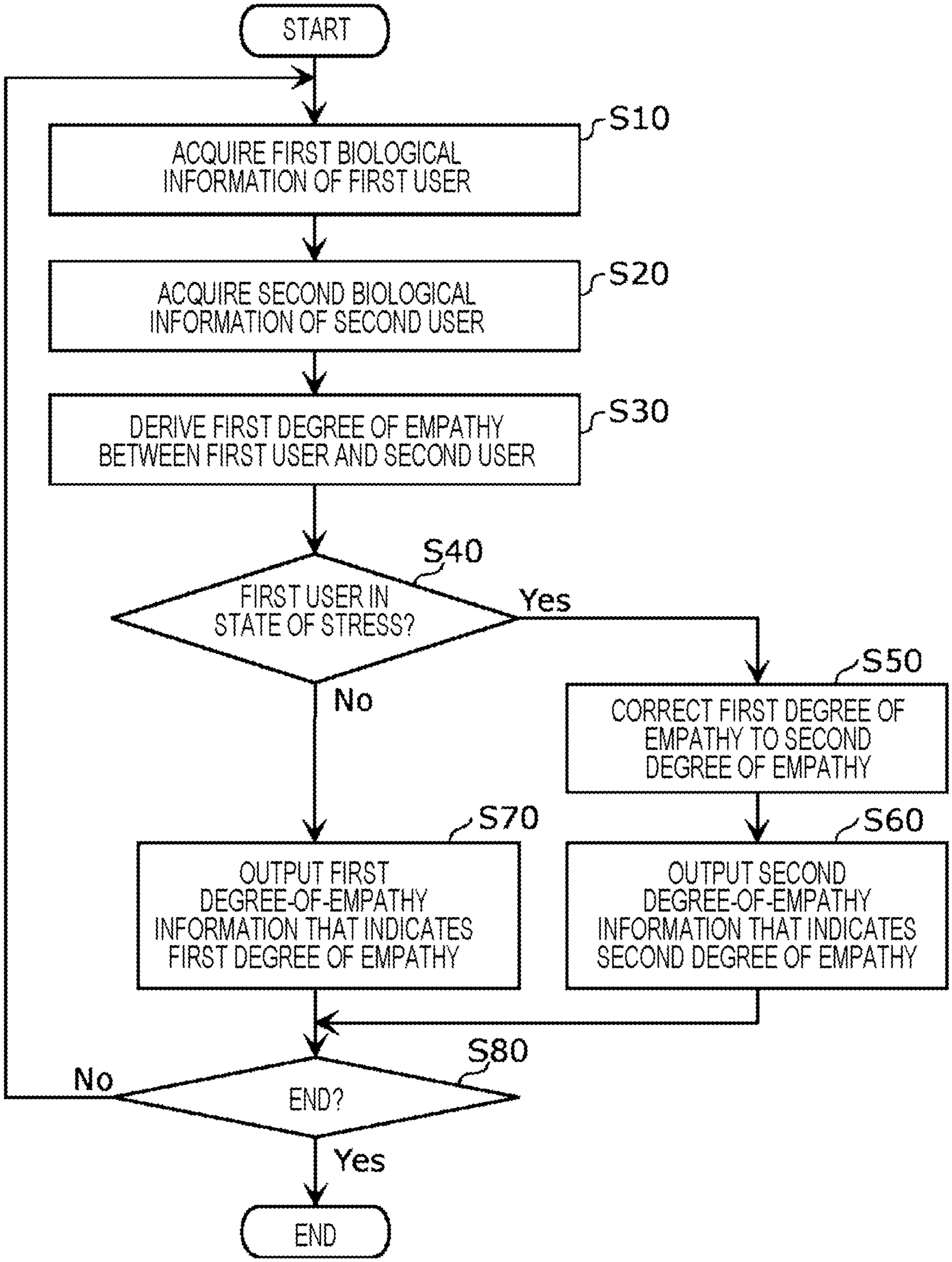
FIG. 8B is a flow chart showing another example of a processing operation of the server according to the embodiment.

FIG. 8B is a flow chart showing another example of a processing operation of the server 100 according to the present embodiment.

As in the case of the example shown in FIG. 8A, the server 100 executes the process in steps S10 to S40. Then, when it is determined in step S40 that the first user is in the state of stress (Yes in step S40), the output processor 105 corrects the first degree of empathy indicated by the first degree-of-empathy information to a second degree of empathy that is higher than the first degree of empathy (step S50). Then, the output processor 105 generates and outputs second degree-of-empathy information that indicates the second degree of empathy (step S60).

On the other hand, when it is determined in step S40 that the first user is not in the state of stress (No in step S40), the output processor 105 outputs the first degree of empathy information without correcting the first degree-of-empathy indicated by the first degree-of-empathy information (step S70).

After that, as in the case of the example shown in FIG. 8A, the server 100 repeatedly executes the process from step S70 on.

Degree-of-Empathy Analyzer

In the following, specific aspects of the degree-of-empathy analyzer 101 according to the present embodiment are described in detail with the inclusion of the processing operation of the sensor 201 and the bioanalyzer 202 of each terminal device 200.

Aspect 1 of Degree-of-Empathy Analyzer

Figure 9:
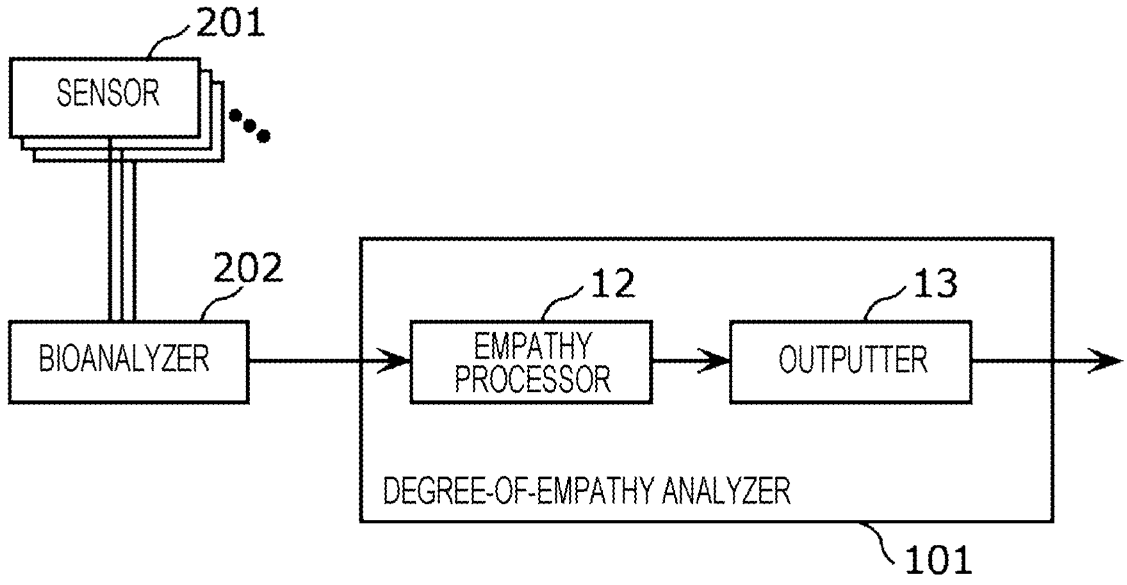
FIG. 9 is a block diagram showing a configuration of a degree-of-empathy analyzer according to Aspect 1 of the embodiment.

FIG. 9 is a block diagram showing a configuration of a degree-of-empathy analyzer 101 according to the present aspect.

The degree-of-empathy analyzer 101 according to the present aspect estimates a degree of empathy between a plurality of persons on the basis of sensing information of the plurality of persons as obtained by a plurality of sensors 201. Such a degree-of-empathy analyzer 101 according to the present aspect includes an empathy processor 12 and an outputter 13.

The bioanalyzer 202 of a terminal device 200 acquires information on the heartbeat of each of the plurality of persons as heartbeat information. This heartbeat information is an example of the aforementioned biological information. Specifically, the bioanalyzer 202 acquires the sensing information of each of the plurality of persons from the plurality of sensors 201 and, by analyzing the sensing information, acquires heartbeat information of that person from the sensing information. Each of the sensors 201 includes, for example, a camera that, by photographing a person, generates a facial image of the person as sensing information. The facial image is, for example, a moving image showing the face of the person. In this case, the bioanalyzer 202 acquires, by video pulse wave extraction from the facial image, heartbeat information that indicates the RRI, heart rate, or heartbeat fluctuation of the person. That is, the bioanalyzer 202 acquires the heartbeat information on the basis of a change in chromaticity of the skin of the face of the person shown in the facial image. The RRI, the heart rate, or the heartbeat fluctuation indicated by the heartbeat information may be an average taken over a period of approximately 1 to 5 minutes.

The RRI is a heartbeat interval (R-R interval) that is an interval between the peaks of two consecutive heartbeat R waves.

The hear rate is, for example, the number of pulsations per minute, and is a number that is calculated by dividing 60 seconds by the number of seconds of RRI.

The heartbeat fluctuation is, for example, a coefficient of variation of R-R intervals (CvRR). The CvRR is a coefficient of variation of heartbeat variation and is calculated, for example, by "CvRR=Standard Deviation SD of RRI over Given Period of Time)/(Average of RRIs over Given Period of Time)". That is, the CvRR is calculated by normalizing the standard deviation SD of RRI over a given period of time by the average of RRIs over the given period of time.

The heartbeat fluctuation may be a high frequency (HF) or a low frequency (LF). The HF and the LF are calculated from power spectra obtained by conducting frequency analyses of equally spaced time-series data of RRI with the use of fast Fourier transform (FFT). The HF is the integral of a power spectrum in a high-frequency domain of 0.14 Hz to 0.4 Hz and is considered to reflect an amount of parasympathetic activity. Further, the LF is the integral of a power spectrum in a low-frequency domain of 0.04 Hz to 0.14 Hz and is considered to reflect amounts of sympathetic and parasympathetic activity. The FFT frequency transform may be performed at intervals of five seconds.

The sensor 201 is not limited to the camera but may include a wearable device that measures an electrocardiogram or a pulse wave. The wearable device includes a phototransistor and a photodiode and may measure a pulse wave by measuring a change in the amount of blood in blood vessels with reflected light or transmitted light. Moreover, the wearable device outputs a result of measurement of the pulse wave as sensing information to the bioanalyzer 202. The bioanalyzer 202 acquires, from such sensing information, heartbeat information that indicates the RRI, heart rate, or CvRR of the person.

The empathy processor 12 derives the degree of empathy between the plurality of persons on the basis of a correlation between changes in heartbeat information of the plurality of persons as acquired by the bioanalyzer 202.

The outputter 13 outputs degree-of-empathy information that indicates the degree of empathy derived by the empathy processor 12.

Figure 10:
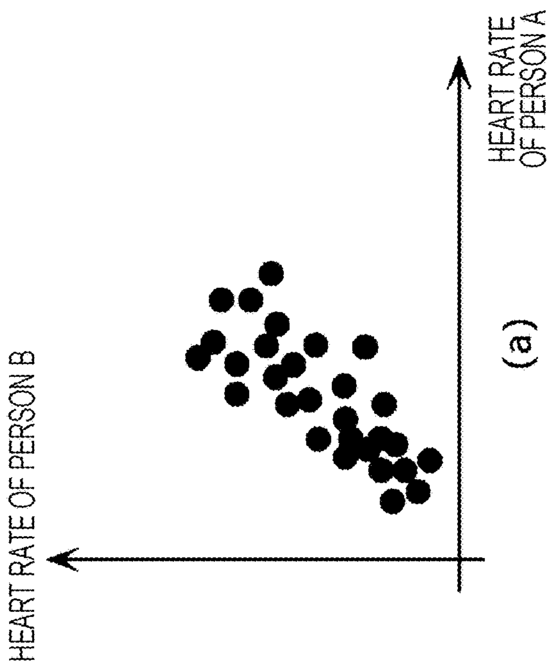
FIG. 10 illustrates diagrams for explaining examples of pieces of heartbeat information of two persons that are acquired by a bioanalyzer according to Aspect 1 of the embodiment and a correlation between those pieces of heartbeat information.

FIG. 10 illustrates diagrams for explaining examples of pieces of heartbeat information of two persons that are acquired by the bioanalyzer 202 and a correlation between those pieces of heartbeat information. Specifically, (a) of FIG. 10 is a graph showing the heart rates of a person A and a person B in a predetermined period of time, and (b) of FIG. 10 shows a relationship between a coefficient of correlation between the pieces of heartbeat information of the plurality of persons and correlation strength.

As shown in (a) of FIG. 10, the bioanalyzer 202 acquires the heart rate of the person A and the heart rate of the person B as heartbeat information. The graph shown in (a) of FIG. 10 has a horizontal axis representing the heart rate of the person A and a vertical axis representing the heart rate of the person B. Further, the graph shown in (a) of FIG. 10 contains dots each of which indicates the heart rates of the persons A and B at substantially the same timing.

For example, for each period of 30 seconds to 2 minutes, the empathy processor 12 analyzes a correlation of heartbeat information between the person A and the person B in that period. That is, the empathy processor 12 periodically performs a process of calculating a coefficient of correlation from time-series data of the heart rates of the persons A and B. As a result of this, temporal changes in coefficient of correlation are grasped.

The empathy processor 12 derives a degree of empathy between the person A and the person B from the coefficient of correlation thus calculated. For example, in a case where the sign of the coefficient of correlation between the person A and the person B is positive and the coefficient of correlation is higher than a threshold, the empathy processor 12 derives a degree of empathy that indicates that the person A and the person B empathize with each other.

As shown in (b) of FIG. 10, a relationship between a coefficient of correlation r and correlation strength may be used. For example, in a case where the coefficient of correlation r is lower than or equal to 0.2, the coefficient of correlation indicates that there is almost no correlation. Further, in a case where the coefficient of correlation r is higher than 0.2 and lower than or equal to 0.4, the coefficient of correlation r indicates that there is a weak correlation. Moreover, in a case where the coefficient of correlation r is higher than 0.4 and lower than or equal to 0.7, the coefficient of correlation r indicates that there is a correlation.

Accordingly, in a case where the coefficient of correlation is higher than 0.4, the empathy processor 12 may derive a degree of empathy that indicates that the person A and the person B empathize with each other. In this case, the threshold is 0.4. The empathy processor 12 may use the threshold to derive a degree of empathy that assumes one or the other of two values of 0 and 1. That is, in a case where the coefficient of correlation is higher than the threshold, the empathy processor 12 derives Degree of Empathy=1, which indicates that the person A and the person B empathize with each other, and in a case where the coefficient of correlation is lower than or equal to the threshold, the empathy processor 12 derives Degree of Empathy=0, which indicates that the person A and the person B do not empathize with each other.

Further, as shown in FIG. (b) of 10, the empathy processor 12 may derive, as a degree of empathy, any one of five levels that correspond to values of the coefficient of correlation. For example, the five levels are set for the coefficient of correlation r such that Level 1<Level 2<Level 3<Level 4<Level 5. In such a case, the empathy processor 12 derives Level 3 as a degree of empathy, for example, if the coefficient of correlation r is higher than 0.4 and lower than or equal to 0.7. Alternatively, the empathy processor 12 may derive, as a degree of empathy, a value obtained by multiplying the coefficient of correlation by 100 or any of numerical values 0 to 100 obtained by inputting the coefficient of correlation to a transfer function.

Figure 11A:
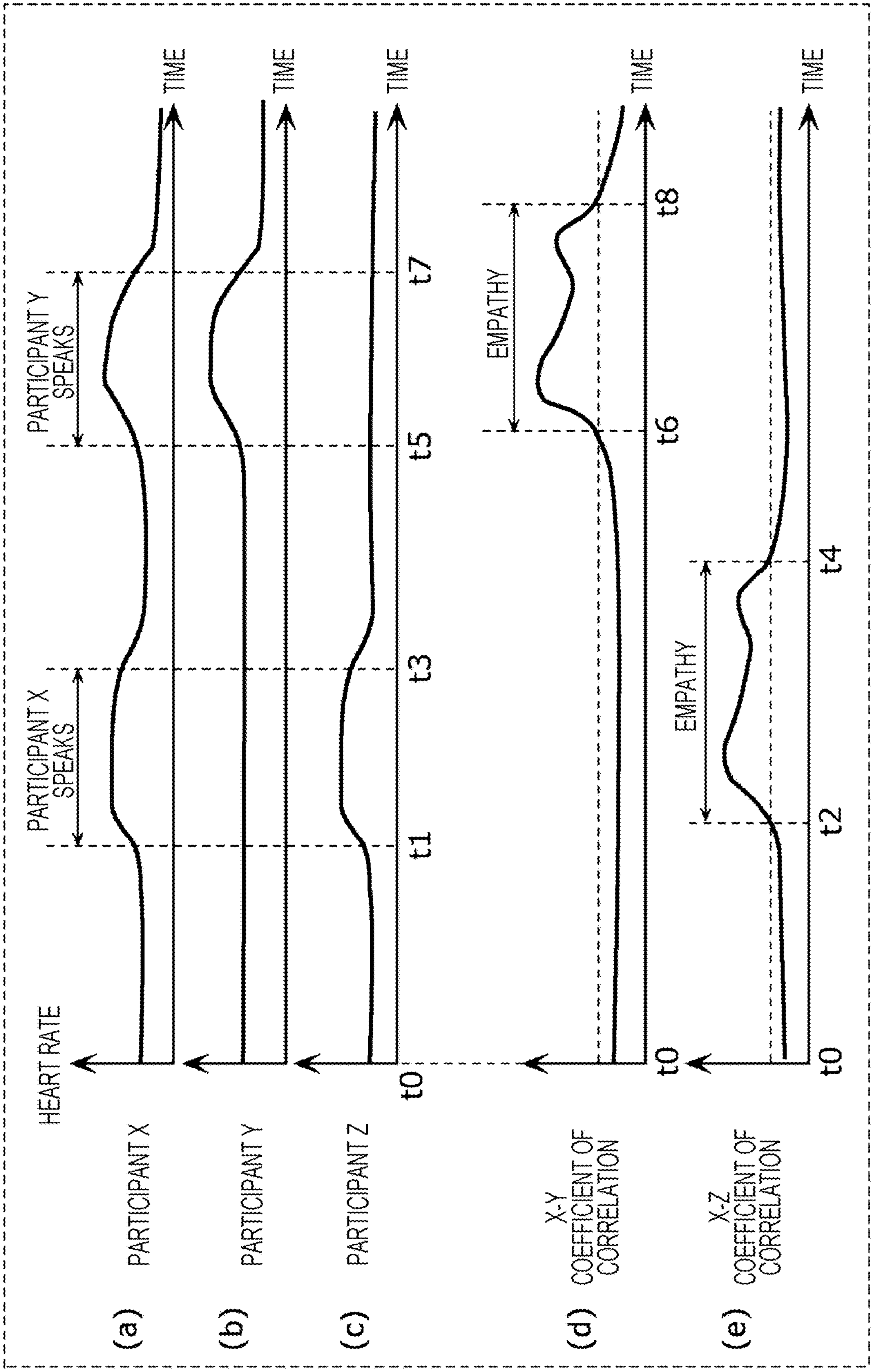
FIG. 11A is a diagram showing temporal changes in heart rate of participants in online communication and temporal changes in coefficient of correlation between two participants according to Aspect 1 of the embodiment.

FIG. 11A is a diagram showing temporal changes in heart rate of participants in online communication and temporal changes in coefficient of correlation between two participants. Specifically, (a) to (c) of FIG. 11A are graphs showing temporal changes in heart rate indicated by heartbeat information of participants X, Y, and Z, respectively. Each of these graphs has a horizontal axis representing time and a vertical axis representing the heart rate. Further, (d) of FIG. 11A is a graph showing temporal changes in coefficient of correlation between the participant X and the participant Y, and (e) of FIG. 11A is a graph showing temporal changes in coefficient of correlation between the participant X and the participant Z. Each of these graphs has a horizontal axis representing time and a vertical axis representing the coefficient of correlation.

When a conference is being held, the bioanalyzer 202 periodically acquires heartbeat information that indicates the hear rates of the participants X, Y, and Z as shown in (a) to (c) of FIG. 11A. On the basis of the heartbeat information of the participants X and Y, the empathy processor 12 periodically calculates the coefficient of correlation between the participant X and the participant Y shown in (d) of FIG. 11A. Similarly, on the basis of the heartbeat information of the participants X and Z, the empathy processor 12 periodically calculates the coefficient of correlation between the participant X and the participant Z shown in (e) of FIG. 11A.

For example, as shown in (a) to (c) of FIG. 11A, when the participant X speaks during times t1 to t3, the heart rates of the participants X and Z rise in the period during which the participant X is speaking, and the heart rate of the participant Y hardly changes in the period. In such a case, as shown in (e) of FIG. 11A, the coefficient of correlation between the participant X and the participant Z becomes higher than the threshold during times t2 to t4 that correspond to the period. Accordingly, the empathy processor 12 derives a degree of empathy that indicates that the participant X and the participant Z empathize with each other during the times t2 to t4. That is, the empathy processor 12 estimates that the participant X and the participant Z empathize with each other during the times t2 to t4. On the other hand, as shown in (d) of FIG. 11A, the coefficient of correlation between the participant X and the participant Y is lower than or equal to the threshold even while the participant X is speaking. Accordingly, the empathy processor 12 derives a degree of empathy that indicates that the participant X and the participant Y do not empathize with each other in the period during which the participant X is speaking. That is, the empathy processor 12 estimates that the participant X and the participant Y do not empathize with each other.

Further, for example, as shown in (a) to (c) of FIG. 11A, when the participant Y speaks during times t5 to t7, the heart rates of the participants X and Y rise in the period during which the participant Y is speaking, and the heart rate of the participant Z hardly changes in the period. In such a case, as shown in (d) of FIG. 11A, the coefficient of correlation between the participant X and the participant Y becomes higher than the threshold during times t6 to t8 that correspond to the period. Accordingly, the empathy processor 12 derives a degree of empathy that indicates that the participant X and the participant Y empathize with each other during the times t6 to t8. That is, the empathy processor 12 estimates that the participant X and the participant Y empathize with each other during the times t6 to t8. On the other hand, as shown in (e) of FIG. 11A, the coefficient of correlation between the participant X and the participant Z is lower than or equal to the threshold even while the participant Y is speaking. Accordingly, the empathy processor 12 derives a degree of empathy that indicates that the participant X and the participant Z do not empathize with each other in the period during which the participant Y is speaking. That is, the empathy processor 12 estimates that the participant X and the participant Z do not empathize with each other.

The empathy processor 12 may identify a speaker by performing speaker recognition, for example, on the basis of an output signal (i.e. voice data) from the microphone of the terminal device 200. Alternatively, in a case where a user ID is associated with voice data that is sent from each terminal device 200, the empathy processor 12 may identify a speaker on the basis of the user ID. Alternatively, the empathy processor 12 may identify a speaker by performing an image recognition process on a facial image serving as sensing information that is obtained from each sensor 201. In this case, the facial image is sent from the terminal device 200 to the server 100. For example, during the times t1 to t3, the participant X is identified as a speaker. Accordingly, when the empathy processor 12 estimates that as shown in (e) of FIG. 11A, the participant X and the participant Z empathize with each other during the times t2 to t4, which partly overlap the period during which the participant X is speaking, the empathy processor 12 determines that the two persons empathize with remarks made by the participant X. In this case, a direction of empathy from the participant Z to the participant X is identified. Similarly, during the times t5 to t7, the participant Y is identified as a speaker. Accordingly, when the empathy processor 12 estimates that as shown in (d) of FIG. 11A, the participant X and the participant Y empathize with each other during the times t6 to t8, which partly overlap the period during which the participant Y is speaking, the empathy processor 12 determines that the two persons empathize with remarks made by the participant Y. In this case, a direction of empathy from the participant X to the participant Y is identified. The outputter 13 may output information that indicates such a direction of empathy.

Thus, in the present aspect, the bioanalyzer 202 acquires heartbeat information of a plurality of persons during an identical period. For example, as mentioned above, the bioanalyzer 202 acquires heartbeat information of the participants X, Y, and Z during the period from the time t1 to the time t3 and acquires heartbeat information of the participants X, Y, and Z during the period from the time t5 to the time t. This makes it possible to properly estimate a degree of empathy of a plurality of persons during an identical period.

Further, instead of deriving a degree of empathy on the basis of a correlation between changes in heartbeat information, the degree-of-empathy analyzer 101 according to the present aspect may derive a degree of empathy on the basis of facial expressions of a plurality of persons.

Figure 11B:
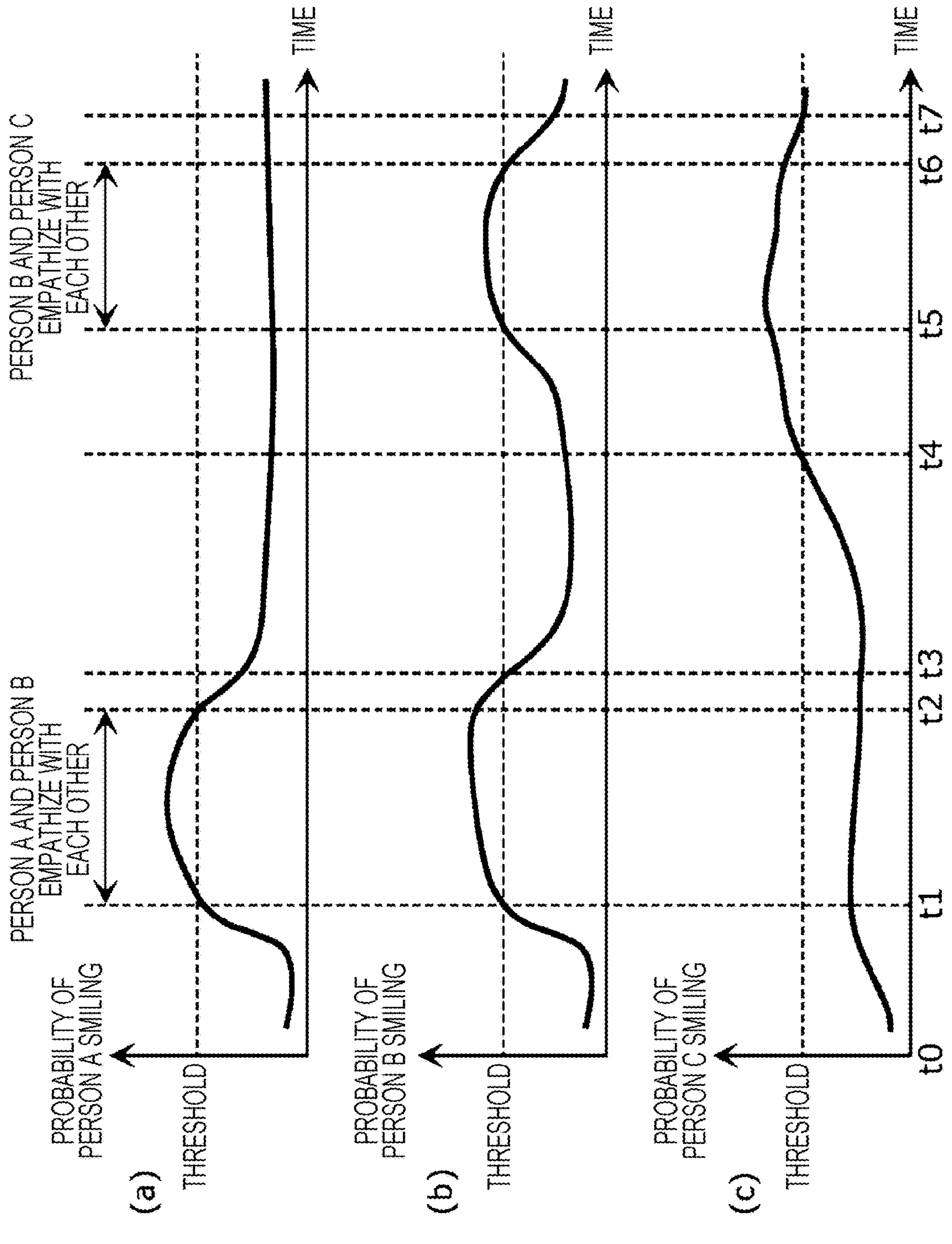
FIG. 11B is a diagram for explaining an example of derivation of a degree of empathy based on a facial expression according to Aspect 1 of the embodiment.

FIG. 11B is a diagram for explaining an example of derivation of a degree of empathy based on a facial expression. (a) of FIG. 11B is a graph showing temporal changes in probability of a person A smiling. (b) of FIG. 11B is a graph showing temporal changes in probability of a person B smiling. (c) of FIG. 11B is a graph showing temporal changes in probability of a person C smiling.

For example, for each of the persons A, B, and C, the degree-of-empathy analyzer 101 acquires a facial image serving as sensing information showing the face of that person. By performing image recognition on the facial image, the empathy processor 12 identifies a facial expression of the face of the person shown in the facial image. Alternatively, by inputting the facial image to a learning model subjected to machine learning, the empathy processor 12 identifies a facial expression of the face of the person shown in the facial image. For example, the empathy processor 12 identifies a probability of smiling as the person's facial expression in chronological order.

As a result of that, for example, as shown in (a) of FIG. 11B, the probability of the person A smiling is identified as being higher than or equal to a threshold during the period from time t1 to time t2. Further, for example, as shown in (b) of FIG. 11B, the probability of the person B smiling is identified as being higher than or equal to the threshold during the period from the time t1 to time t3 and the period from time t5 to time t6. Further, for example, as shown in (c) of FIG. 11B, the probability of the person C smiling is identified as being higher than or equal to a threshold during the period from time t4 to time t7. Accordingly, the degree-of-empathy analyzer 101 determines that the person A and the person B empathize with each other during the period from the time t1 to the time t2, during which the probability of the person A smiling and the probability of the person B smiling are both higher than or equal to the threshold. Similarly, the degree-of-empathy analyzer 101 determines that the person B and the person C empathize with each other during the period from the time t5 to the time t6, during which the probability of the person B smiling and the probability of the person C smiling are both higher than or equal to the threshold. As a result of that, the degree-of-empathy analyzer 101 may derive 1 (or 100) as a degree of empathy between the person A and the person B during the period from the time t1 to the time t2 and derive 1 (or 100) as a degree of empathy between the person B and the person C during the period from the time t5 to the time t6.

Alternatively, the degree-of-empathy analyzer 101 according to the present aspect may derive a degree of empathy on the basis of facial expressions of a plurality of persons as well as a correlation between changes in heartbeat information. That is, first, as mentioned above, the empathy processor 12 identifies the facial expressions of the plurality of persons by performing image recognition on facial images. Then, the empathy processor 12 derives a degree of empathy between the plurality of persons on the basis of a correlation between changes in heartbeat information of the plurality of persons and the facial expressions thus identified of the plurality of persons.

For example, the empathy processor 12 identifies any of a delightful facial expression, an angry facial expression, a sorrowful facial expression, and a joyful facial expression. Alternatively, the empathy processor 12 may identify these four facial expressions as numerical values. In this case, a person's facial expression is expressed as a vector composed of four numerical values. As a result of this, the facial expressions of the plurality of persons are identified. Then, the empathy processor 12 derives a degree of similarly of the facial expressions of the plurality of persons. The degree of similarity may be derived as a numerical value of 0 to 1. The empathy processor 12 may derive a degree of empathy between the plurality of persons, for example, by multiplying the average of the degree of similarity and the coefficient of correlation by 100.

Since a degree of empathy is thus derived on the basis of facial expressions as well as a correlation between changes in heartbeat information, estimate accuracy of the degree of empathy can be improved. Further, the facial expressions of the plurality of persons can be identified from sensing information of the sensors 201 used for acquiring the heartbeat information. That is, those facial expressions are identified from video data (i.e. the aforementioned facial images) of the cameras. This makes it possible to omit a dedicated device for identifying those facial expressions. This makes it possible to simplify the entire system configuration.

Further, although, in the aforementioned example, facial expressions are identified from facial images, facial expressions may be identified from voice data. In this case, the empathy processor 12 acquires voice data that is outputted from the microphone of each terminal device 200 and, by analyzing the voice data, identifies facial expressions of the plurality of persons. The analysis may involve the use of machine learning. The facial expressions may be identified by the empathy processor 12 as mentioned above, or may be identified by the bioanalyzer 202.

Further, from the voice data, mental states such as persons' emotions such as delight, anger, sorrow, and joy, relaxation, or excitement may be estimated. For example, in a case where two participants are estimated to be in the same mental state at the same timing, the empathy processor 12 derives a high degree of empathy as a degree of empathy between the two participants.

Further, a degree of empathy may be derived using, instead of or together with facial expressions, other biological information reflecting mental states. The other biological information may be data that represents, for example, the acceleration of a person's motion, the temperature of the face, or the amount of perspiration of the hand. The temperature of the face may be measured by a thermocouple or may be measured by infrared thermography. Further, the amount of perspiration may be measured by an electrode attached to the hand. This makes it possible to further improve estimate accuracy of the degree of empathy.

Figure 12:
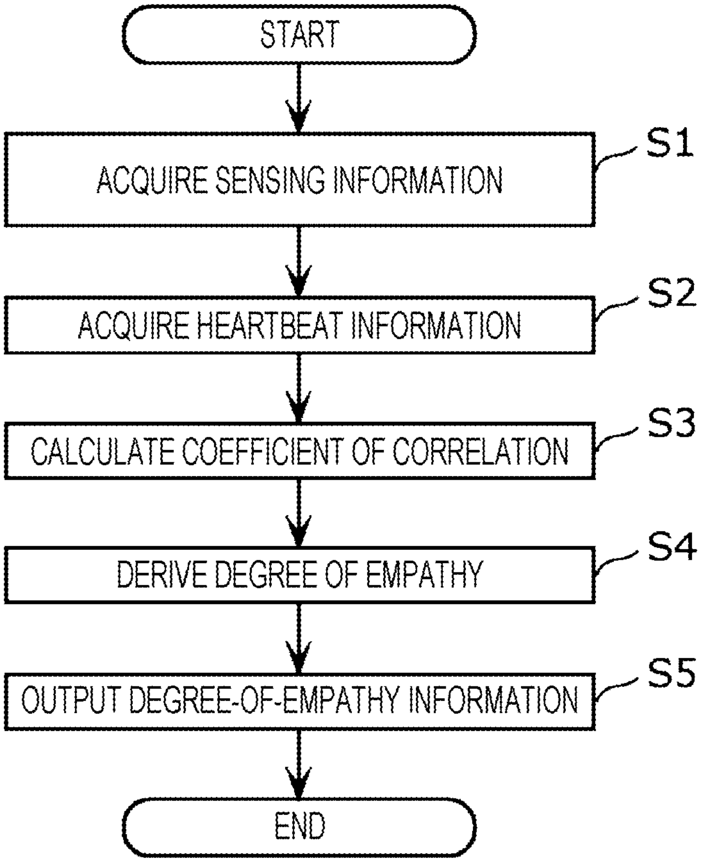
FIG. 12 is a flow chart showing a processing operation of the bioanalyzer and the degree-of-empathy analyzer according to Aspect 1 of the embodiment.

FIG. 12 is a flow chart showing a processing operation of the bioanalyzer 202 and the degree-of-empathy analyzer 101 according to the present aspect.

First, the bioanalyzer 202 acquires sensing information of each of the plurality of persons from the plurality of sensors 201 (step S1). Then, the bioanalyzer 202 acquires, from the sensing information, heartbeat information that indicates a heart rate, an RRI, or a heartbeat fluctuation (step S2). As a result of this, heartbeat information of each of the plurality of persons is acquired.

Next, the empathy processor 12 calculates a coefficient of correlation based on changes in heartbeat information of each of the plurality of persons (step S3) and derives a degree of empathy from the coefficient of correlation (step S4).

Then, the outputter 13 outputs degree-of-empathy information that indicates the degree of empathy thus derived (step S5).

As noted above, the degree-of-empathy analyzer 101 according to the present aspect derives a degree of empathy between a plurality of persons on the basis of a correlation between changes in heartbeat information on the heartbeat of each of the plurality of persons. Moreover, the degree-of-empathy analyzer 101 outputs degree-of-empathy information that indicates the degree of empathy thus derived. This makes it possible to properly estimate the degree of empathy, which is an emotional interaction that takes place between the plurality of persons.

Further, the bioanalyzer 202 according to the present aspect acquires heartbeat information that indicates a heart rate, an RRI, or a heartbeat fluctuation. However, the heartbeat information may indicate at least one of the heart rate and the heartbeat fluctuation. Alternatively, the bioanalyzer 202 may acquire heartbeat information that indicates at least two of the heart rate, the RRI, and the heartbeat fluctuation. In this case, the empathy processor 12 may calculate the average of at least two of a coefficient of correlation between heart rates, a coefficient of correlation between RRIs, and a coefficient of correlation between heartbeat fluctuations and derive a degree of empathy from the average. This makes it possible to improve estimate accuracy of the degree of empathy.

Further, although the empathy processor 12 of the degree-of-empathy analyzer 101 according to the present aspect derives a degree of empathy on the basis of a coefficient of correlation between heartbeat information of each of the plurality of persons and heartbeat information of the other, the empathy processor 12 may derive a degree of empathy on the basis of a correlation between changes in heartbeat information without calculating the coefficient of correlation. For example, the empathy processor 12 may derive a degree of empathy of the plurality of persons on the basis of a degree of coincidence of the timings of changes in heartbeat information of the plurality of persons. The timings are, for example, timings at which the heart rates or other parameters rise or fall. Further, the empathy processor 12 may derive a degree of empathy of the plurality of persons on the basis of a degree of coincidence of periods during which the heat rates of the plurality of persons are higher than reference values. The reference values are values of the heart rates set separately for each of the persons and, for example, are each the average heart rate of that person in a period during which the person is in a resting state.

Aspect 2 of Degree-of-Empathy Analyzer

A degree-of-empathy analyzer 101 according to the present aspect determines factors of stress of a plurality of persons and derives a degree of empathy between a plurality of persons on the basis of those factors. For example, heartbeat information according to the present aspect indicates an RRI and a CvRR. Moreover, an amount of change in RRI that indicates a change in RRI and an amount of change in CvRR that indicates a change in CvRR are used. For each of the plurality of persons, the degree-of-empathy analyzer 101 determines a factor of stress of that person on the basis of the amounts of change in RRI and change in CvRR of that person. Moreover, if the plurality of persons have a common factor of stress, the degree-of-empathy analyzer 101 estimates that the plurality of persons empathize with each other, as there is some correlation with the factor of stress. On the other hand, if the plurality of persons have no common factor of stress, the degree-of-empathy analyzer 101 estimates that the plurality of persons do not empathize with each other, as there is no correlation with any factor of stress.

Figure 13:
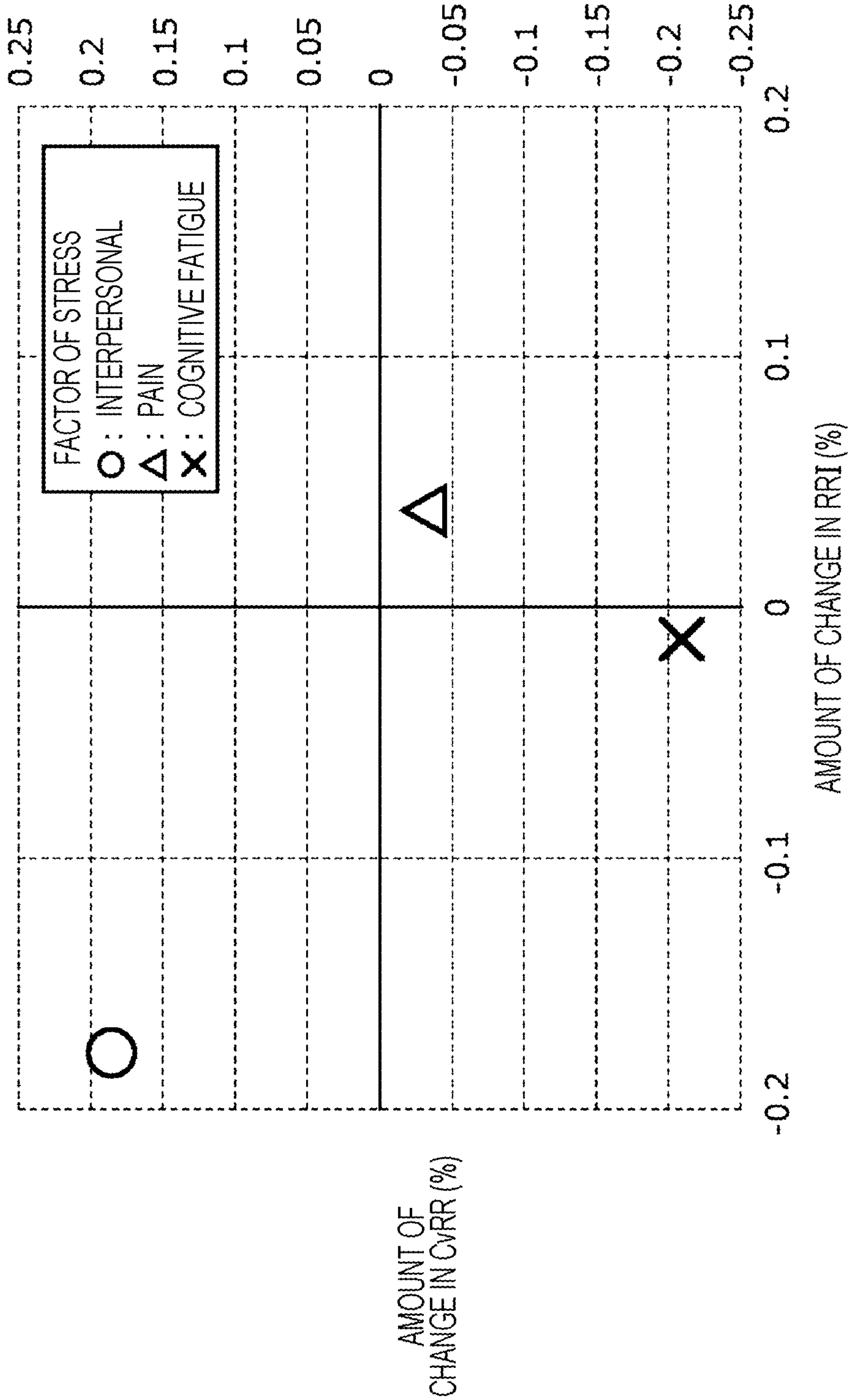
FIG. 13 is a graph obtained by an experiment and a diagram showing a relationship between amounts of change in RRI and change in CvRR and factors of stress according to Aspect 2 of the embodiment.

FIG. 13 is a graph obtained by an experiment and a diagram showing a relationship between amounts of change in RRI and change in CvRR and factors of stress. The graph shown in FIG. 13 has a horizontal axis representing the amount of change in RRI (%) and a vertical axis representing the amount of change in CvRR (%).

It is confirmed by the experiment that the amounts of change in RRI and change in CvRR of a person vary depending on factors of stress of the person. In the experiment, twenty subjects were each assigned three types of task with different factors of stress, and the RRIs and CvRRs of the subjects were measured while the subjects were executing the tasks. The three types of task are a task that causes interpersonal stress, a task that causes stress pertaining to pain, and a task that causes stress pertaining to cognitive fatigue.

The amount of change in RRI (%) was calculated according to "Amount of Change in RRI={(Average of RRIs during Execution of Task)−(Average of RRIs during Rest)}/(Average of RRIs during Rest)×100 (Formula 1)". An RRI during rest is an RRI measured for five minutes prior to execution of a task by a subject with the subject in the same position as he/she was in when executing the task. Moreover, the average of RRIs during rest is the average of RRIs over a period of 60 seconds to 240 seconds after the start of measurement. The average of RRIs during execution of the task is the average of RRIs over a period of 60 seconds to 240 seconds after the start of measurement out of RRIs measured while the subject was executing the task.

The amount of change in CvRR (%) was calculated according to "Amount of Change in CvRR={(Average of CvRRs during Execution of Task)−(Average of CvRRs during Rest)}/(Average of CvRRs during Rest)×100 (Formula 2)". A CvRR during rest is a CvRR measured for five minutes prior to execution of a task by a subject with the subject in the same position as he/she was in when executing the task. Moreover, the average of CvRRs during rest is the average of CvRRs over a period of 60 seconds to 240 seconds after the start of measurement. The average of CvRRs during execution of the task is the average of CvRRs over a period of 60 seconds to 240 seconds after the start of measurement out of CvRRs measured while the subject was executing the task.

The graph shown in FIG. 13 shows the average of the amounts of change in RRI and the average of the amounts of change in CvRR of the twenty subjects for each type of task, i.e. for each factor of stress. The circle in the graph indicates the average of the amounts of change in RRI and the average of the amounts of change in CvRR of the twenty subjects in the case of a factor of stress "INTERPERSONAL". Further, the triangle in the graph indicates the average of the amounts of change in RRI and the average of the amounts of change in CvRR of the twenty subjects in the case of a factor of stress "PAIN". Further, the X in the graph indicates the average of the amounts of change in RRI and the average of the amounts of change in CvRR of the twenty subjects in the case of a factor of stress "COGNITIVE FATIGUE".

Accordingly, the degree-of-empathy analyzer 101 according to the present aspect determines factors of stress of a plurality of persons with the use of the relationship shown in FIG. 13 between the amounts of change in RRI and change in CvRR and the factors of stress. As in the case of Aspect 1, the degree-of-empathy analyzer 101 according to the present aspect is configured as shown in FIG. 9. Further, as in the case of Aspect 1, each of the sensors 201 may include a camera or may include a wearable device. The bioanalyzer 202 according to the present aspect acquires pieces of sensing information from the plurality of sensors 201 and, for each of the plurality of persons, acquires, from those pieces of sensing information, heartbeat information that indicates the RRI and CvRR of that person.

Figures 14, 15:
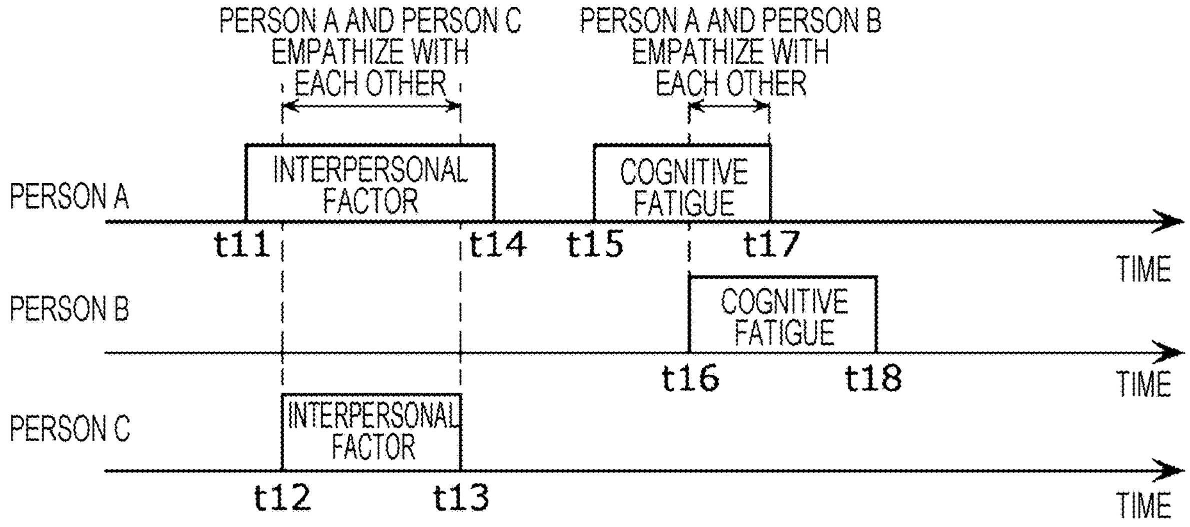
FIG. 14 is a diagram for explaining a method for determination of a factor of stress by an empathy processor according to Aspect 2 of the embodiment.
FIG. 15 is a diagram showing an example in which degrees of empathy are derived from factors of stress of a plurality of persons according to Aspect 2 of the embodiment.

FIG. 14 is a diagram for explaining a method for determination of a factor of stress by an empathy processor 12.

The empathy processor 12 of the degree-of-empathy analyzer 101 calculates the amounts of change in RRI and change in CvRR of each of the plurality of persons according to the aforementioned Formulas 1 and 2. The tasks in Formulas 1 and 2 may be any types of task. Moreover, as shown in FIG. 14, the empathy processor 12 determines a factor of stress on the basis of those amounts of change.

For example, in a case where the RRI of a person is much lower than it was during rest and the CvRR of the person is much higher than it was during rest, the empathy processor 12 determines that the factor of stress of the person is "INTERPERSONAL". Further, in a case where the RRI of a person is a bit higher than it was during rest and the CvRR of the person is almost the same as it was during rest, the empathy processor 12 determines that the factor of stress of the person is "PAIN". Further, in a case where the RRI of a person is almost the same as it was during rest and the CvRR of the person is much lower than it was during rest, the empathy processor 12 determines that the factor of stress of the person is "COGNITIVE FATIGUE".

Specifically, a positive first threshold and a negative second threshold are set for the amount of change in RRI, and a positive third threshold and a negative fourth threshold are set for the amount of change in CvRR. In this case, in a case where the amount of change in RRI of a person is lower than the negative second threshold and the amount of change in CvRR of the person is higher than or equal to the positive third threshold, the empathy processor 12 determines that the factor of stress of the person is "INTERPERSONAL".

Further, in a case where the amount of change in RRI of a person is higher than or equal to the positive first threshold and the amount of change in CvRR of the person is lower than the positive third threshold and is higher than or equal to the negative fourth threshold, the empathy processor 12 determines that the factor of stress of the person is "PAIN".

Further, in a case where the amount of change in RRI of a person is lower than the positive first threshold and is higher than or equal to the negative second threshold and the amount of change in CvRR of the person is lower than the negative fourth threshold, the empathy processor 12 determines that the factor of stress of the person is "COGNITIVE FATIGUE".

FIG. 15 is a diagram showing an example in which degrees of empathy are derived from factors of stress of a plurality of persons.

The degree-of-empathy analyzer 101 determines factors of stress of persons A, B, and C, for example, on the basis of heartbeat information of those persons. Specifically, the degree-of-empathy analyzer 101 determines that the factor of stress of the person A during times t11 to t14 is "INTERPERSONAL" and determines that the factor of stress of the person A during times t15 to t17 is "COGNITIVE FATIGUE". Further, the degree-of-empathy analyzer 101 determines that the factor of stress of the person B during times t16 to t18 is "COGNITIVE FATIGUE". Further, the degree-of-empathy analyzer 101 determines that the factor of stress of the person C during times t12 to t13 is "INTERPERSONAL".

In such a case, since there is a coincidence of factor of stress between the person A and the person C during the period from the time t12 to the time t13, the empathy processor 12 of the degree-of-empathy analyzer 101 estimates that the person A and the person C empathize with each other during the period. That is, the empathy processor 12 derives, for example, "1" as a degree of empathy between the person A and the person C during the times t12 to t13. Similarly, since there is a coincidence of factor of stress between the person A and the person B during the period from the time t12 to the time t17, the empathy processor 12 estimates that the person A and the person B empathize with each other during the period. That is, the empathy processor 12 derives, for example, "1" as a degree of empathy between the person A and the person B during the times t16 to t17. The empathy processor 12 may derive a degree of empathy among the three persons A, B, and C. For example, for each period, the empathy processor 12 derives the average of a degree of empathy between the person A and the person B during that period, a degree of empathy between the person A and the person C during that period, and a degree of empathy between the person B and the person C during that period as the degree of empathy among the three persons.

The outputter 13 outputs degree-of-empathy information that indicates the degree of empathy thus derived.

As noted above, the degree-of-empathy analyzer 101 according to the present aspect calculates the amounts of change in RRI and change in CvRR of each of the plurality of persons and, on the basis of a correlation between factors of stress determined from those amounts of change, derives a degree of empathy between the plurality of persons. That is, even in the present aspect, the degree of empathy between the plurality of persons is derived on the basis of a correlation between changes in heartbeat information of the plurality of persons. Accordingly, also in the present aspect, the degree of empathy, which is an emotional interaction that takes place between the plurality of persons, can be properly estimated.

Aspect 3 of Degree-of-Empathy Analyzer

In each of Aspects 1 and 2, the degree-of-empathy analyzer 101 derives a degree of empathy with the use of heartbeat information. In the present aspect, a degree of empathy is derived with the use of SC information as well as heartbeat information. The SC information is biological information other than the heartbeat of each of a plurality of persons. The SC information is information that indicates the skin conductance of a fingertip of a person. The skin conductance is hereinafter also called an "SC".

Figures 16, 17:
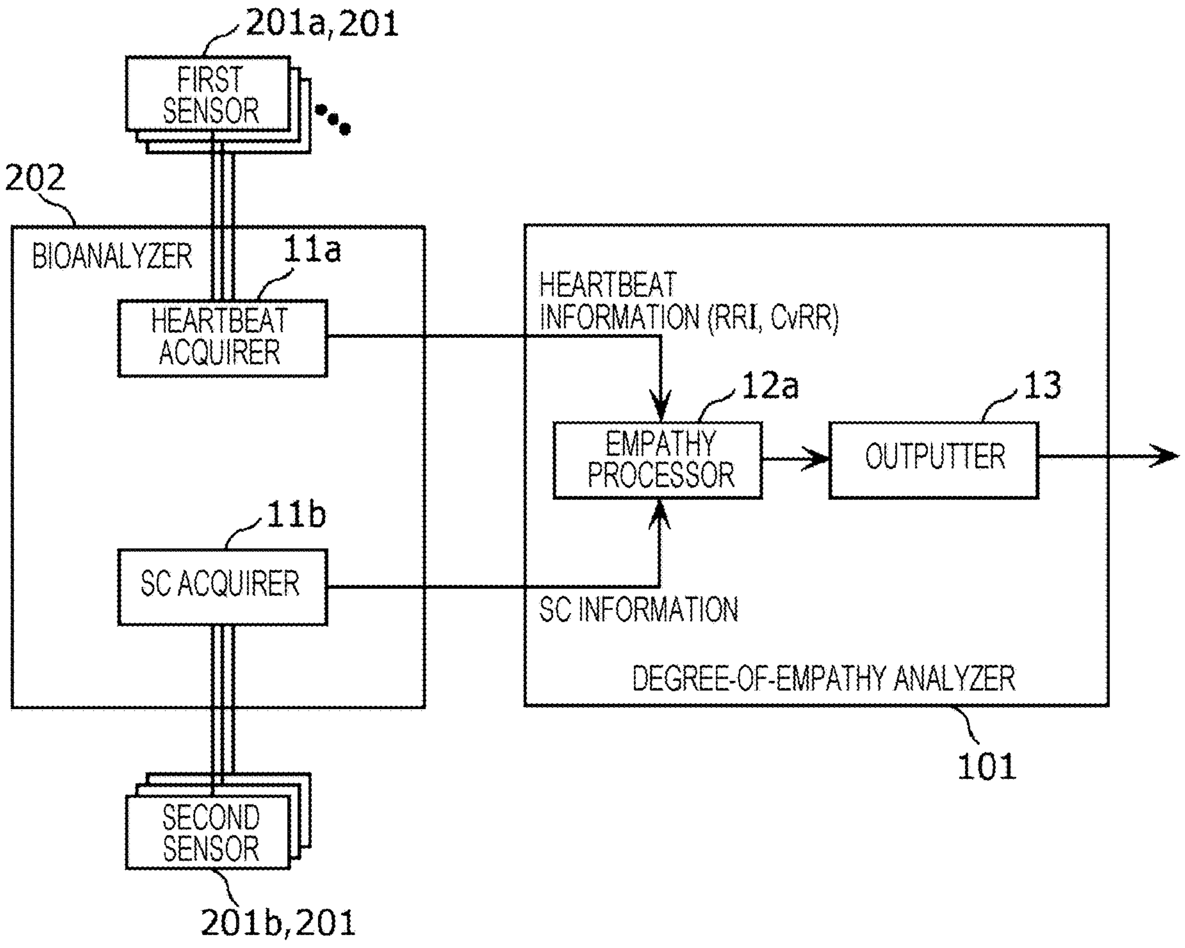
FIG. 16 is a block diagram showing configurations of a bioanalyzer and a degree-of-empathy analyzer according to Aspect 3 of the embodiment.
FIG. 17 is a diagram for explaining a method for determination of a factor of stress by an empathy processor according to Aspect 3 of the embodiment.

FIG. 16 is a block diagram showing configurations of a bioanalyzer 202 and a degree-of-empathy analyzer 101 according to the present aspect.

The degree-of-empathy analyzer 101 according to the present aspect estimates a degree of empathy between a plurality of persons on the basis of heartbeat information and SC information. In the present aspect, the bioanalyzer 202 includes a heartbeat acquirer 11*a* and an SC acquirer 11*b*, and the degree-of-empathy analyzer 101 includes an empathy processor 12*a* and an outputter 13.

As with the bioanalyzers 202 of Aspects 1 and 2, the heartbeat acquirer 11*a* acquires information on the heartbeat of a person as heartbeat information. Specifically, the heartbeat acquirer 11*a* acquires first sensing information of each of the plurality of persons from a plurality of sensors 201*a* and, by analyzing the first sensing information, acquires heartbeat information of that person from the first sensing information. As with the sensors 201 of Aspects 1 and 2, each of the first sensor 201*a* is a camera that, by photographing a person, generates a facial image of the person as first sensing information. The first sensor 201*a* is not limited to the camera but may be a wearable device that measures an electrocardiogram or a pulse wave. The heartbeat acquirer 11*a* according to the present aspect acquires, from the first sensing information of each of the plurality of persons, heartbeat information that indicates the RRI and CvRR of that person.

The SC acquirer 11*b* acquires SC information of a person. Specifically, the SC acquirer 11*b* acquires second sensing information of each of the plurality of persons from a plurality of second sensors 201*b* and, by analyzing the second sensing information, acquires SC information of that person from the second sensing information. Each of the second sensors 201*b* is, for example, a sensor including a pair of sensing electrodes, is wound around a fingertip of a person, and outputs, as second sensing information, information that indicates a potential of the skin of the fingertip. The SC acquirer 11*b* according to the present aspect analyzes the second sensing information of each of the plurality of persons and thereby acquires SC information that indicates the skin conductance of that person. The first sensors 201*a* and the second sensors 201*b* may be included in the sensors 201 of the foregoing embodiment.

As in the case of Aspect 2, the empathy processor 12*a* calculates the amounts of change in RRI and change in CvRR of a person on the basis of heartbeat information acquired by the heartbeat acquirer 11*a*. Furthermore, the empathy processor 12*a* according to the present aspect calculates the amount of change in skin conductance of a person on the basis of SC information acquired by the SC acquirer 11*b*. The amount of change in skin conductance is hereinafter also called an "amount of change in SC".

Specifically, the empathy processor 12*a* calculates the amount of change in SC according to "Amount of Change in SC={(Average of SCs during Execution of Task)−(Average of SCs during Rest)}/(Average of SCs during Rest)×100 (Formula 3)". An SC during rest is an SC measured for five minutes prior to execution of a task by a person with the person in the same position as he/she was in when executing the task. Moreover, the average of SCs during rest is the average of SCs over a period of 60 seconds to 240 seconds after the start of measurement. The average of SCs during execution of the task is the average of SCs over a period of 60 seconds to 240 seconds after the start of measurement out of SCs measured while the person was executing the task. Further, the task in Formula 3 may be any type of task.

Moreover, the empathy processor 12*a* determines a factor of stress on the basis of the amount of change in RRI, the amount of change in CvRR, and the amount of change in SC. Furthermore, the empathy processor 12*a* derives a degree of empathy between the plurality of persons on the basis of a factor of stress of each of the plurality of persons.

As in the case of Aspects 1 and 2, the outputter 13 outputs degree-of-empathy information that indicates the degree of empathy derived by the empathy processor 12*a*.

FIG. 17 is a diagram for explaining a method for determination of a factor of stress by the empathy processor 12*a*.

For example, in a case where the RRI of a person is lower than it was during rest, the CvRR of the person is higher than it was during rest, and the SC of the person is higher than it was during rest, the empathy processor 12*a* determines that the factor of stress of the person is "INTERPERSONAL". Further, in a case where the RRI of a person is higher than it was during rest, the CvRR of the person is almost the same as it was during rest, and the SC of the person is higher than it was during rest, the empathy processor 12*a* determines that the factor of stress of the person is "PAIN". Further, in a case where the RRI of a person is almost the same as it was during rest, the CvRR of the person is lower than it was during rest, and the SC of the person is almost the same as it was during rest, the empathy processor 12*a* determines that the factor of stress of the person is "COGNITIVE FATIGUE".

Specifically, a positive first threshold and a negative second threshold are set for the amount of change in RRI, a positive third threshold and a negative fourth threshold are set for the amount of change in CvRR, and a positive fifth threshold and a negative sixth threshold are set for the amount of change in SC. In this case, in a case where (a) the amount of change in RRI of a person is lower than the negative second threshold, (b) the amount of change in CvRR of the person is higher than or equal to the positive third threshold, and (c) the amount of change in SC of the person is higher than or equal to the positive fifth threshold, the empathy processor 12*a* determines that the factor of stress of the person is "INTERPERSONAL".

Further, in a case where (a) the amount of change in RRI of a person is higher than or equal to the positive first threshold, (b) the amount of change in CvRR of the person is lower than the positive third threshold and is higher than or equal to the negative fourth threshold, and (c) the amount of change in SC of the person is higher than or equal to the positive fifth threshold, the empathy processor 12*a* determines that the factor of stress of the person is "PAIN".

Further, in a case where (a) the amount of change in RRI of a person is lower than the positive first threshold and is higher than or equal to the negative second threshold, (b) the amount of change in CvRR of the person is lower than the negative fourth threshold, and (c) the amount of change in SC of the person is lower than the positive fifth threshold and is higher than or equal to the negative sixth threshold, the empathy processor 12*a* determines that the factor of stress of the person is "COGNITIVE FATIGUE".

Figure 18:
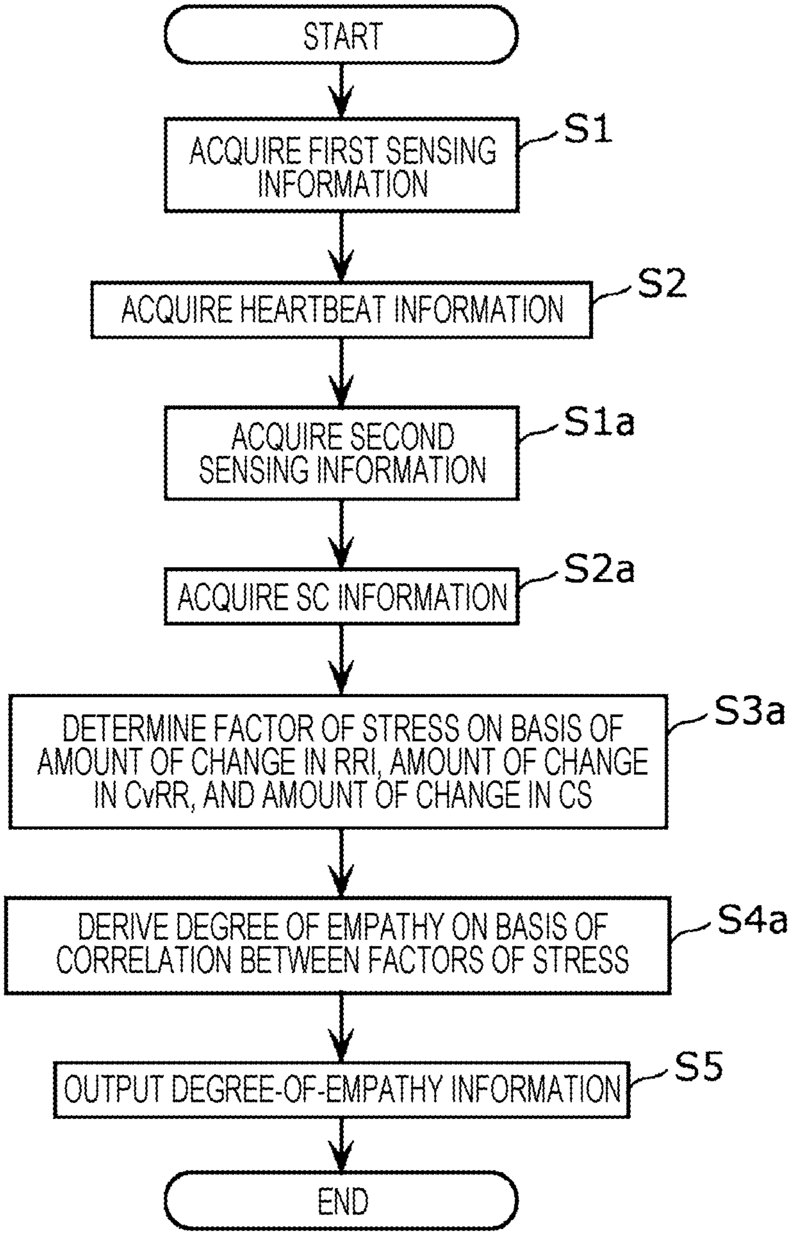
FIG. 18 is a flow chart showing a processing operation of the bioanalyzer and the degree-of-empathy analyzer according to Aspect 3 of the embodiment.

FIG. 18 is a flow chart showing a processing operation of the bioanalyzer 202 and the degree-of-empathy analyzer 101.

First, the heartbeat acquirer 11*a* of the bioanalyzer 202 acquires first sensing information of each of the plurality of persons from the plurality of first sensors 201*a* (step S1). Then, the heartbeat acquirer 11*a* acquires, from the first sensing information, heartbeat information that indicates an RRI and a CvRR (step S2). As a result of this, heartbeat information of each of the plurality of persons is acquired.

Next, the SC acquirer 11*b* acquires second sensing information of each of the plurality of persons from the plurality of second sensors 201*b* (step S1*a*). Then, the SC acquirer 11*b* acquires, from the second sensing information, SC information that indicates an SC (step S2*a*). As a result of this, SC information of each of the plurality of persons is acquired.

Next, the empathy processor 12*a* calculates the amounts of change in RRI, change in CvRR, and change in SC of each of the plurality of persons and, on the basis of those amounts of change, determines a factor of stress of each of the plurality of persons (step S3*a*). Furthermore, the empathy processor 12*a* derives a degree of empathy between the plurality of persons on the basis of a correlation between the factors of stress of the plurality of persons, i.e. whether the plurality of persons have an identical factor in common (step S4*a*).

Then, the outputter 13 outputs degree-of-empathy information that indicates the degree of empathy thus derived (step S5).

As noted above, the degree-of-empathy analyzer 101 according to the present aspect calculates the amounts of change in RRI, change in CvRR, and change in SC of each of the plurality of persons and, on the basis of a correlation between factors of stress determined from those amounts of change, derives a degree of empathy between the plurality of persons. That is, even in the present aspect, the degree of empathy between the plurality of persons is derived on the basis of a correlation between changes in heartbeat information of the plurality of persons. Accordingly, also in the present aspect, the degree of empathy, which is an emotional interaction that takes place between the plurality of persons, can be properly estimated. Further, in the present aspect, as compared with Aspect 2, since the amount of change SC is used for determining a factor of stress, determination accuracy of the factor of stress can be improved. As a result of that, estimate accuracy of the degree of empathy can be improved.

Instead of including the SC acquirer 11*b*, which acquires the skin conductance of a person, the bioanalyzer 202 according to the present aspect may include a constituent element that acquires the skin temperature of a person. In this case, each of the second sensors 201*b* is, for example, a thermocouple. Further, the empathy processor 12*a* calculates the amount of change in skin temperature instead of the amount of change in SC. Specifically, the empathy processor 12*a* calculates the amount of change in skin temperature according to "Amount of Change in Skin Temperature={(Average of Skin Temperatures during Execution of Task)−(Average of Skin Temperatures during Rest)}/(Average of Skin Temperatures during Rest)×100 (Formula 4)". A skin temperature during rest is a skin temperature measured for five minutes prior to execution of a task by a person with the person in the same position as he/she was in when executing the task. Moreover, the average of skin temperatures during rest is the average of skin temperatures over a period of 60 seconds to 240 seconds after the start of measurement. The average of skin temperatures during execution of the task is the average of skin temperatures over a period of 60 seconds to 240 seconds after the start of measurement out of skin temperatures measured while the person was executing the task. Further, the task in Formula 4 may be any type of task. The empathy processor 12*a* determines a factor of stress using such an amount of change in skin temperature instead of the amount of change in SC.

User State Analyzer

The following describes in detail a specific aspect of determination of a state of stress of a first user by the user state analyzer 107 according to the present embodiment.

As in the case of Aspect 2 or 3 of the aforementioned degree-of-empathy analyzer 101, the user state analyzer 107 determines a factor of stress in determining whether the first user is in a state of stress. For example, the user state analyzer 107 determines the factor of stress with the use of the amount of change in RRI and the amount of change in CvRR according to the method for determining a factor of stress shown in FIG. 14. Alternatively, the user state analyzer 107 determines the factor of stress with the use of the amount of change in RRI, the amount of change in CvRR, and the amount of change in SC according to the method for determining a factor of stress shown in FIG. 17. Moreover, in a case where any of the factors of stress "INTERPERSONAL", "PAIN", and "COGNITIVE FATIGUE" has been determined, the user state analyzer 107 determines that the first user is in the state of stress. On the other hand, in a case where none of the factors of stress "INTERPERSONAL", "PAIN", and "COGNITIVE FATIGUE" has been determined, the user state analyzer 107 determines that the first user is not in the state of stress.

Further, when the user state analyzer 107 determines that the first user is in the state of stress, the user state analyzer 107 may derive the extend of the state of stress as a degree of stress. For example, in a case where the factor of stress of the first user is "INTERPERSONAL", the user state analyzer 107 derives a larger value as the degree of stress when the amount of decrease in RRI of the first user is larger and the amount of rise in CvRR of the first user is larger. Alternatively, in a case where the factor of stress of the first user is "INTERPERSONAL", the user state analyzer 107 derives a larger value as the degree of stress when the amount of decrease in RRI of the first user is larger, the amount of rise in CvRR of the first user is larger, and the amount of rise in SC of the first user is larger.

For example, in a case where the factor of stress of the first user is "PAIN", the user state analyzer 107 derives a larger value as the degree of stress when the amount of rise in RRI of the first user is larger and the amount of change in CvRR of the first user is smaller. Alternatively, in a case where the factor of stress of the first user is "PAIN", the user state analyzer 107 derives a larger value as the degree of stress when the amount of rise in RRI of the first user is larger, the amount of change in CvRR of the first user is smaller, and the amount of rise in SC of the first user is larger.

For example, in a case where the factor of stress of the first user is "COGNITIVE FATIGUE", the user state analyzer 107 derives a larger value as the degree of stress when the amount of change in RRI of the first user is smaller and the amount of decrease in CvRR of the first user is larger. Alternatively, in a case where the factor of stress of the first user is "COGNITIVE FATIGUE", the user state analyzer 107 derives a larger value as the degree of stress when the amount of change in RRI of the first user is smaller, the amount of decrease in CvRR of the first user is larger, and the amount of change in SC of the first user is smaller.

The degree of stress thus derived may be reflected in the magnitude of a correction value for the first degree of empathy. That is, in correcting the first degree of empathy, the output processor 105 may add a larger correction value to the first degree of empathy when the degree of stress is higher and add a smaller correction value to the first degree of empathy when the degree of stress is lower.

Other Modifications

Although the foregoing has described an information processing system and an information processing method according to one or more aspects of the present disclosure with reference to the foregoing embodiment, the present disclosure is not limited to the foregoing embodiment. Applications to the foregoing embodiment of various modifications conceived of by persons skilled in the art may as well be encompassed in the present disclosure, as long as such applications do not depart from the scope of the present disclosure.

For example, although, in the foregoing embodiment, a correction value is added to the first degree of empathy when the first user is in a state of stress and a correction value is added to the first degree of empathy also in a case where the first user is in a state of poor relationship, the correction values in those two cases may be different from each other. Further, the correction values in those two cases may be determined by methods that are different from each other. For example, in one of the two cases, a value obtained by adding a random number to a predetermined value may be determined as a correction value, and in the other case, a correction value that corresponds to the magnitude of the first degree of empathy may be determined without using a random number.

Further, although, in the foregoing embodiment, the server 100 determines whether the first user is in a state of stress and determines whether the relationship between the first user and the second user is good, the server 100 may determine, in addition to these determinations, whether to output the second degree-of-empathy information. For example, the output processor 105 may determine whether the first degree of empathy is higher than a certain standard and, on the basis of a result of the determination, whether to output the first degree-of-empathy information or output the second degree-of-empathy information. Specifically, in a case where the first degree of empathy is higher than or equal to a predetermined threshold, the output processor 105 may determine that the first degree of empathy is higher than a certain standard and output the first degree-of-empathy information. For example, there can be a case where a high first degree of empathy is derived even if the first user is in a state of tension or the human relationship between the first user and the second user is not good. In such a case, even outputting the first degree-of-empathy information without correcting the first degree of empathy poses little risk of inhibiting communication between the two persons. Accordingly, as mentioned above, in a case where whether the first degree of empathy is higher than a standard is determined and the first degree of empathy is higher than the standard, a load of a process of generating the second degree-of-empathy information can be reduced by outputting the first degree-of-empathy information without generating the second degree-of-empathy information.

Further, although, in the foregoing embodiment, the output processor 105 is provided in the server 100, the output processor 105 may be provided in the terminal device 200. Further, each terminal device 200 may include not only the output processor 105 but also all or some of the constituent elements provided in the server 100. On the other hand, the server 100 may include all or some of the constituent elements provided in the terminal device 200.

Further, although, in the foregoing embodiment, online communication is performed, non-online face-to-face communication may be performed. For example, when a conference is held in a conference room, each attendee gathering in the conference room may grasp a degree of empathy with another attendee by operating the terminal device 200 while having communication face to face.

Further, in Aspect 1 of the degree-of-empathy analyzer 101, a degree of empathy is derived from a coefficient of correlation, and in Aspects 2 and 3, a degree of empathy is derived from a factor of stress. However, the degree-of-empathy analyzer 101 may calculate the average of a degree of empathy derived from a coefficient of correlation and a degree of empathy derived from a factor of stress and output, as final degree-of-empathy information, degree-of-empathy information that indicates the average. Furthermore, a degree of empathy may also be derived with the use of other biological information other than heartbeat information. As mentioned above, the other biological information may be data that represents, for example, a facial expression, the acceleration of a person's motion, the temperature of the face, or the amount of perspiration of the hand. In a case where the heartbeat information according to Aspect 1 indicates a heartbeat fluctuation, the heartbeat fluctuation may be LF/HF, which is considered to indicate an amount of sympathetic activity. Further, although the amount of change in RRI, the amount of change in CvRR, the amount of change in SC, and the amount of change in skin temperature according to Aspects 2 and 3 may be expressed as ratios as shown in Formulas 1 to 4, respectively, these amounts of change may be expressed as differences.

In the foregoing embodiment, each constituent element may be constituted by dedicated hardware or may be implemented by executing a software program suited to that constituent element. Each constituent element may be implemented by a program executor such as a central processing unit (CPU) or a processor reading out and executing a software program stored on a storage medium such as a hard disk or a semiconductor memory. Software that implements the foregoing embodiment is a program that causes a computer to execute each step of the flow charts shown in FIGS. 8A and 8B.

According to the embodiment described above, in a case where the first user is in a state of stress, second degree-of-empathy information that indicates a degree of empathy that is higher than the degree of empathy indicated by the first degree-of-empathy information may be outputted, and also in a case where the first user is in a state of poor relationship, the second degree-of-empathy information may be outputted. However, in a case where an utterance condition pertaining to the amount of utterance of the first user is satisfied, second degree-of-empathy information that indicates a degree of empathy that is lower than the first degree of empathy may be outputted. Whether the utterance condition is satisfied may be determined, for example, on the basis of voice data pertaining to a voice of at least either the first user or the second user. The voice data may be acquired from a microphone. The utterance condition may be a condition pertaining to how large the amount of utterance of the first user is. For example, in a case where the amount of utterance of the first user is larger than or equal to a threshold in a certain period of time, it may be determined that the utterance condition is satisfied. In a case where the amount of utterance of the first user is smaller than the threshold in a certain period of time, it may be determined that the utterance condition is not satisfied. Further, the utterance condition may be a condition pertaining to a comparison between how large the amount of utterance of the first user is and how large the amount of utterance of the second user is. Specifically, in a case where the amount of utterance of the first user in a certain period of time is larger than the amount of utterance of the second user in the period of time, it may be determined that the utterance condition is satisfied. For example, in a case where the amount of utterance of the first user is twice or more times or three or more times as large as the amount of utterance of the second user, it may be determined that the amount of utterance of the first user is larger than the amount of utterance of the second user. Without being bound by this, the ratio of the amount of utterance of the first user to the amount of utterance of the second user pertaining to a condition for determining that the amount of utterance of the first user is larger than the amount of utterance of the second user can be arbitrarily set.

The amount of utterance may be an amount that indicates the number of utterances or may be an amount that indicates the length of utterance. Alternatively, the amount of utterance may be an amount obtained by combining the number of utterances and the length of utterance. For example, the amount of utterance may be an amount that indicates the product of the number of utterances and the length of utterance.

For the derivation of the amount of utterance of the first user or the amount of utterance of the second user on the basis of voice data, for example, information on the first user's voice and information on the second user's voice may be stored in a terminal storages or a server storage. Performing a process of associating information on the user's voices stored with a voice indicated by voice data outputted from a microphone makes it possible to determine which user has produced an utterance, making it possible to derive the amount of utterance of the first user and the amount of utterance of the second user. The method for determining which user has produced an utterance is disclosed, for example, in Japanese Unexamined Patent Application Publication No. 2021-164060.

As described above, in a case where the utterance condition pertaining to the amount of utterance of the first user is satisfied, second degree-of-empathy information that indicates a degree of empathy that is lower than the first degree of empathy may be outputted. In other words, in a case where the amount of utterance by a particular user is large, a degree of empathy that is lower than an actual degree of empathy is fed back to the particular user. This causes the user to recognize that he/she has lowered the degree of empathy by producing an unilateral utterance, making it possible to reduce unilateral utterances and facilitate interactive communication between the users. This makes it possible to more smoothly perform communication.

The process of, in a case where the utterance condition pertaining to the amount of utterance of the first user is satisfied, outputting second degree-of-empathy information that indicates a degree of empathy that is lower than the first degree of empathy may be combined with at least either the process of, in a case where the first user is in a state of stress, outputting second degree-of-empathy information that indicates a degree of empathy that is higher than the degree of empathy indicated by the first degree-of-empathy information or the process of, in a case where the first user is in a state of poor relationship, outputting second degree-of-empathy information that indicates a degree of empathy that is higher than the degree of empathy indicated by the first degree-of-empathy information.

In the embodiment described above, the relationship information may be voice data. Alternatively, the relationship information may be text data. The text data can, for example, be data that represents text that corresponds to a message or a chat inputted by the first user and/or the second user. The text data may be generated, for example, on the basis of information inputted to an input device such as a keyboard or a game machine controller. Online communication between users may be not only performed with voice data but also performed with text data. The terms "conversation" and "utterance" as used herein encompass not only acts that are conducted with voice but also acts that are conduced with text.

In another aspect, the relationship information may be affiliation data on an organization and/or a community to which the first user and the second user belong. In this case, for example, if the first user and the second user belong to an identical organization for a period of time longer than or equal to a threshold, it may be determined that the relationship between the first user and the second user is good. Alternatively, in a case where the first user and the second user manipulate their respective avatars to communicate with each other in a virtual space, the relationship data may be data that represents a situation of participation in an event in the virtual space. For example, the number of times the first user and the second user participate in an identical event is larger than or equal to a threshold, it may be determined that the relationship between the first user and the second user is good.

Further, in another aspect, the relationship information may be attribute data that represents attributes of the first user and the second user. The attributes may include information, for example, on gender, age, and occupation. In this case, for example, if the number of attributes that the first user and the second user have in common is higher than or equal to a threshold, it may be determined that the relationship between the first user and the second user is good.

It should be noted that the present disclosure also encompasses the following cases.

(1) The at least one device is specifically a computer system composed of a microprocessor, a read-only memory (ROM), a random-access memory (RAM), a hard disk unit, a display unit, a keyboard, a mouse, or other components. The RAM or the hard disk unit has a computer program stored therein. A function of the at least one device is achieved by the microprocessor operating in accordance with the computer program. To achieve the predetermined function, the computer program is constituted by a combination of command codes that indicate instructions for a computer.

(2) The at least one device may be constituted by constituent elements all or some of which are constituted by one system large-scale integration (LSI). The system LSI is a super-multifunction LSI fabricated by integrating a plurality of components on one chip and, specifically, is a computer system composed of a microprocessor, a ROM, a RAM, or other components. The RAM has a computer program stored therein. A function of the system LSI is achieved by the microprocessor operating in accordance with the computer program.

(3) The at least one device may be constituted by constituent elements all or some of which are constituted by an IC card or a single module that can be attached to and detached from the device. The IC card or the module is a computer system composed of a microprocessor, a ROM, a RAM, or other components. The IC card or the module may include the aforementioned super-multifunction LSI. A function of the IC card or the module is achieved by the microprocessor operating in accordance with a computer program. The IC card or the module may have tamper resistance.

(4) The present disclosure may be directed to the aforementioned methods. Further, these methods may be directed to computer programs that are implemented by computers or may be directed to digital signals composed of computer programs.

Further, the present disclosure may be directed to a computer program or a digital signal stored on a computer-readable storage medium such as a flexible disk, a hard disk, a CD (Compact Disc)-ROM, a DVD, a DVD-ROM, a DVD-RAM, a BD (Blu-ray (registered trademark) Disc), or a semiconductor memory. The present disclosure may also be directed to digital signals stored on these storage media.

Further, the present disclosure may be directed to the transmission of a computer program or a digital signal via a telecommunication line, a wireless or wired communication line, a network typified by the Internet, data broadcasting, or other routes.

Further, a program or a digital signal may be executed by another independent computer either by storing the program or the digital signal on a storage medium and transferring the program or the digital signal or by transferring the program or the digital signal via a network or other routes.

The present disclosure is applicable, for example, to a communication system that is used in communication among a plurality of persons.

What is claimed is:

1. An online communication system comprising;

a first camera that detects light from a first user and generates a first video showing a face of the first user;

a second camera that detects light from a plurality of second users communicating with the first user during an online conference via a communication network and generates second videos showing faces of the second users during the online conference; and a processing apparatus, wherein the processing apparatus, during the online conference:

generates, based on the first video, first biological data relating to a heartbeat of the first user by using pulse wave extraction to analyze changes in chromaticity of the skin of the face of the first user;

generates, based on the second videos, second biological data relating to a heartbeat of each of the second users by using pulse wave extraction to analyze changes in chromaticity of the skin of the faces of the second users;

analyzes a correlation between the heartbeat of the first user and the heartbeat of each of the second users based on the first biological data and the second biological data to obtain a plurality of correlations;

derives a degree of empathy between the first user and each of the second users based on the plurality of correlations to obtain a plurality of degrees of empathy;

determines, based on the first biological data, whether a heart rate of the first user exceeds a threshold for a certain period of time or longer; and causes a display of the first user to display a display screen image containing a) the second videos showing the faces of the second users, b) a current degree of empathy, and c) a degree-of-empathy graph showing temporal changes in the current degree of empathy over time, wherein:

in a case where the processing apparatus determines that the heart rate of the first user does not exceed the threshold for the certain period of time or longer, the processing apparatus uses a first algorithm to determine the current degree of empathy to include first empathy information based on the plurality of degrees of empathy; and in a case where the processing apparatus determines that the heart rate of the first user exceeds the threshold for the certain period of time or longer, the processing apparatus uses a second algorithm to determine the current degree of empathy to include second empathy information that indicates a higher degree of empathy than does the first empathy information.

2. The online communication system according to claim 1, wherein the second algorithm is an algorithm which adds a positive numerical value to a value indicated by the first empathy information.

3. The communication system according to claim 1, wherein the processing apparatus calculates a respective coefficient of correlation based on the heartbeat of the first user and each second user to obtain a plurality of coefficients of correlation and derives the plurality of degrees of empathy based on the respective plurality of coefficients of correlation.

4. The online communication system according to claim 1, wherein the first biological data and the second biological data include at least one selected from the group consisting of: a heartbeat interval which is an interval between the peaks of R waves of two consecutive heartbeats; CvRR which is a coefficient of variation of heart rate variability; and an integral value of a power spectrum calculated from a power spectrum obtained by frequency analyzing the heartbeat interval using a fast Fourier transform.

5. The online communication system according to claim 1, wherein the processing apparatus generates differential information by calculating a difference between the plurality of degrees of empathy indicated by the first empathy information and the higher degree of empathy indicated by the second empathy information.

6. The online communication system according to claim 1, wherein the processing apparatus further identifies a facial expression of the first user by performing image recognition on the first video, the facial expression being a vector of four numerical values representing a delightful facial expression, an angry facial expression, a sorrowful facial expression, and a joyful facial expression;

identifies facial expressions of the second users by performing image recognition on the second videos;

derives a degree of similarity of the facial expressions between the first user and each of the second users; and derives the degree of empathy between the first user and each of the second users based on the respective correlation between the first user and each said second user and the degree of similarity of the facial expressions between the first user and each said second user.

7. An information processing method comprising:

causing a first camera to detect light from a first user and generate a first video showing a face of the first user;

causing a second camera to detect light from a plurality of second users communicating with the first user during an online conference via a communication network and generate second videos showing faces of the second users;

generating, based on the first video, first biological data relating to a heartbeat of the first user by using pulse wave extraction to analyze changes in chromaticity of the skin of the face of the first user;

generating, based on the second videos, second biological data relating to heartbeat of the second users by using pulse wave extraction to analyze changes in chromaticity of the skin of the faces of the second user users;

analyzing a correlation between the heartbeat of the first user and the heartbeat of each of the second users based on the first biological data and the second biological data to obtain a plurality of correlations;

deriving a degree of empathy between the first user and the second users based on the plurality of correlations to obtain a plurality of degrees of empathy;

determining whether or not the first user is in a stressed state based on the first biological data; and causing a display of the first user to display a display screen image containing a) the second videos showing the faces of the second users, b) a current degree of empathy, and c) a degree-of-empathy graph showing temporal changes in the current degree of empathy over time, wherein:

in a case where the processing apparatus determines that the first user is not in a stressed state, the processing apparatus uses a first algorithm to determine the current degree of empathy to include first empathy information based on the plurality of degrees of empathy; and in a case where the processing apparatus determines that the first user is in a stressed state, the processing apparatus uses a second algorithm different from the first algorithm to determine the current degree of empathy to include second empathy information that indicates a higher degree of empathy than does the first empathy information.

8. An A-online communication system comprising;

a first camera that detects light from a first user and generates a first video showing a face of the first user;

a second camera that detects light from a plurality of second users communicating with the first user during an online conference via a communication network and generates second videos showing faces of the second users; and a processing apparatus, wherein the processing apparatus, during the online conference:

generates, based on the first video, first biological data relating to heartbeat of the first user by using pulse wave extraction to analyze changes in chromaticity of the skin of the face of the first user;

generates, based on the second videos, second biological data relating to heartbeat of each of the second users by using pulse wave extraction to analyze changes in chromaticity of the skin of the faces of the second users;

analyzes a correlation between the heartbeat of the first user and the heartbeat of each of the second users based on the first biological data and the second biological data to obtain a plurality of correlations;

derives a degree of empathy between the first user and each of the second users based on the plurality of correlations to obtain a plurality of degrees of empathy;

determines whether or not the first user is in a stressed state based on the first biological data; and causes a display of the first user to display a display screen image containing a) the second videos showing the faces of the second users, b) a current degree of empathy, and c) a degree-of-empathy graph showing temporal changes in the current degree of empathy over time, wherein:

in a case where the processing apparatus determines that the first user is not in a stressed state, the processing apparatus uses a first algorithm to determine the current degree of empathy to include first empathy information based on the plurality of degrees of empathy; and in a case where the processing apparatus determines that the first user is in a stressed state, the processing apparatus uses second algorithm different from the first algorithm to determine the current degree of empathy to include second empathy information that indicates a higher degree of empathy than does the first empathy information.

* * * * *